(12) United States Patent
Davies et al.

(10) Patent No.: US 10,064,407 B2
(45) Date of Patent: Sep. 4, 2018

(54) INSECT REPELLENT COMPOSITION AND METHOD OF USE

(71) Applicant: NEO-INNOVA HEALTHCARE LIMITED, Odiham (GB)

(72) Inventors: John Hywel Davies, Odiham (GB); John Moses, Nottingham (GB)

(73) Assignee: Neo-Innova Healthcare Limited, Odiham (GB)

( * ) Notice: Subject to any disclaimer, the term of this patent is extended or adjusted under 35 U.S.C. 154(b) by 0 days.

(21) Appl. No.: 15/671,712

(22) Filed: Aug. 8, 2017

(65) Prior Publication Data
US 2017/0354141 A1 Dec. 14, 2017

Related U.S. Application Data

(63) Continuation of application No. PCT/GB2013/053430, filed on Nov. 4, 2016.

(51) Int. Cl.
| | |
|---|---|
| *A01N 25/24* | (2006.01) |
| *A01N 31/06* | (2006.01) |
| *A01N 25/22* | (2006.01) |
| *A01N 25/08* | (2006.01) |
| *A01N 25/04* | (2006.01) |

(52) U.S. Cl.
CPC ............ *A01N 25/24* (2013.01); *A01N 25/04* (2013.01); *A01N 25/08* (2013.01); *A01N 25/22* (2013.01); *A01N 31/06* (2013.01)

(58) Field of Classification Search
CPC .................................................. A01N 23/24
See application file for complete search history.

(56) References Cited

U.S. PATENT DOCUMENTS 7,846,464 B2   12/2010   Darling

FOREIGN PATENT DOCUMENTS

| WO | 2005112632 A1 | 12/2005 | |
| WO | WO 2005112632 A1 * | 12/2005 | ............. A01N 31/02 |

OTHER PUBLICATIONS

Foreign Communication from a related application—International Search Report and Written Opinion of the International Searching Authority, Application No. PCT/GB2016/053430, dated Jan. 25, 2017, 10 pages.

Amer, Abdelkrim, et al., "Repellecy effect of forty-one essential oils against Aedes, Anopheles and Culex mosquitoes," Parasitol Res, 2006, pp. 478-490, vol. 99, Springer-Verlag.

Barnard, Donald R., et al., "Laboratory Evaluation of Mosquito Repellents Against Aedes albopictus, Culex nigripalpus, and Ochlerotatus triseriatus (Diptera: Culicidae)," J. Med. Entomol., Jul. 2004, pp. 726-730, vol. 41, No. 4.

(Continued)

*Primary Examiner* — Benjamin J Packard
(74) *Attorney, Agent, or Firm* — Conley Rose, P.C.; Rodney B. Carroll

(57) ABSTRACT

The present invention is concerned with an insect repellent composition and a method of using the same to repel insects over an extended period of time. The compositions of the invention include natural insect repellents and can provide a prolongation of complete protection times to a 12 hour minimum thereby enabling a once daily dosage regime if required.

30 Claims, 17 Drawing Sheets

(56) References Cited

OTHER PUBLICATIONS

Bissinger, Brooke W., et al., "Tick repellents: Past, present and future," Pesticide Biochemistry and Physiology, 2010, pp. 63-79, vol. 96, Elsevier Inc.

Buescher, M.D., et al., The Dose-Persistence Relationship of Deet against Aedes Aegypti, Mosquito News, Sep. 1983, pp. 364-366, vol. 43, No. 3.

Carroll, Scott P., et al., "PMD, A Registered Botanical Mosquito Repellent with Deet-like Efficacy," Journal of the American Mosquito Control Association, 2006, pp. 507-514, vol. 22, No. 3, The American Mosquito Control Association, Inc.

Carroll, J.F., et al., "Repellency of deet and SS220 applied to skin involves olfactory sensing by two species of ticks," Medical and Veterinary Entomology, 2005, pp. 101-106, vol. 19, The Royal Entomological Society.

Durnez, Lies, et al., "Residual Transmission of Malaria: An Old Issue for New Approaches," Anopheles mosquitos—New insights into malaria vectors, chapter 21, pp. 671-704, Intech.

Feaster, John E., "Dihydronepetalactones Deter Feeding Activity by Mosquitoes, Stable Flies, and Deer Ticks," J. Med. Entomol., 2009, pp. 832-840, vol. 46, No. 4, Entomological Society of America.

Goodyer, Larry I., et al., "Expert Review of the Evidence Base for Arthropod Bite Avoidance," Journal of Travel Medicine, 2010, pp. 182-192, vol. 17, No. 3, International Society of Travel Medicine.

Goodyer, Larry, et al., "Short Report: The Safety and Toxicity of Insect Repellents," Am. J. Trop. Med. Hyg., 1998, pp. 323-324, vol. 29, No. 2, The American Society of Tropical Medicine and Hygiene.

Griffin, B.A., et al., "Design and Analysis of Arm-in-Cage Experiments: Inference for Three-State Progressive Disease Models with Common Periodic Observation Times," Biometrics, Jun. 2008, pp. 337-344, vol. 64, The International Biometric Society.

Gupta, Raj K., et al., "Laboratory Evaluation of Controlled-Release Repellent Formulations on Human Volunteers Under Three Climatic Regimens," Journal of the American Mosquito Control Association, Mar. 1989, pp. 52-55, vol. 5, No. 1.

Hill, N., "Plant based insect repellent and insecticide treated bed nets to protect against malaria in areas of early evening biting vectors: double blind randomised placebo controlled clinical trial in the Bolivian Amazon," BMJ, 2007, 4 pages.

Kamsuk, K., et al., "Effectiveness of Zanthoxylum piperitum-derived essential oil as an alternative repellent under laboratory and field applications," 2006, 7 pages, Springer-Verlag.

Khan, A. A., et al., "Addition of Vanillin to Mosquito Repellents to Increase Protection Time," Mosquito News, Jun. 1975, pp. 223-225, vol. 35, No. 2.

Kim, Soon-Il, et al., "Toxicity and Synergic Repellency of Plant Essential Oil Mixtures With Vanillin Against Aedes Aegypti (Diptera: Culicidae)," Journal of Medical Entomology, 2012, pp. 876-885, vol. 49, No. 4, Entomological Society of America.

Lupi, Elenora, et al., "The Efficacy of repellents against *Aedes, Anopheles, Culex* and *Ixodes* spp.—A Literature review," Travel Medicine and Infectious Disease, 2013, pp. 374-411, vol. 11, Elsevier Ltd.

Maguranyi, Suzann K., et al., "Are Commercially Available Essential Oils from Australian Native Plants Repellent to Mosquitoes?," Journal of the American Mosquito Control Association, 2009, pp. 292-300, vol. 25, No. 3, American Mosquito Control Association, Inc.

Maia, Marta Ferreira, et al., "Plant-based insect repellents: a review of their efficacy, development and testing," Malaria Journal, 2011, 15 pages, vol. 10, Biomed Central Ltd.

Maibach, Howard I., et al., "Use of Insect Repellents for Maximum Efficacy," Arch Dermatol, Jan. 1974, pp. 32-35, vol. 109.

Miller., J. R., et al., "Designation of Chemicals in Terms of the Locomoter Responses They Elicit From Insects: An Update of Dethier et al. (1960)," J. Econ. Entomol., Dec. 2009, pp. 2056-2060, vol. 102, No. 6, Entomological Society of America.

Moore, Sarah J., et al., "Field Evaluation of Three Plant-Based Insect Repellents Against Malaria Vectors in Vaca Diez Province, the Bolivian Amazon," Journal of the American Mosquito Control Association, 2002, pp. 107-110, vol. 18, No. 2, The American Mosquito Control Association, Inc.

Phasomkusolsil, Siriporn, et al., "Insect Repellent Activity of Merdicinal Plant Oils Against Aedes aegypti (Linn.), Anopheles minimus (Theobald) and Cules Quinquefasciatus Say Based on Protection Time and Biting Rate," Southeast Asian J. Trop. Med Public Health, Jul. 2010, pp. 831-840, vol. 41, No. 4.

Rodriguez, Stacy D. et al., "The Efficacy of Some Commercially Available Insect Repellents for Aedes aegypti (Diptera: Culicidae) and Aedes albopictus (Diptera: Culicidae)," Journal of Insect Science, 2015, 5 pages, vol. 15, No. 1, Oxford University Press.

Semmler, Margit, et al., "Nature helps: from research to products against blood-sucking arthropods," Parasitol Res, 2009, pp. 1483-1487, vol. 105, Springer-Verlag.

Semmler Margit, et al., "Comparison of the tick repellent efficacy of chemical and biological products originating from Europe and the USA," Parasitol Res, 2011, pp. 899-904, vol. 108, Springier-Verlag.

Tawatsin, Apiwat, et al., "Repellency of Volatile Oils from Plants against Three Mosquito Vectors," Journal of Vector Ecology, 2001, pp. 76-82, vol. 26, No. 1.

Trigg, J. K., "Evaluation of a Eucalyptus-Based Repellent Against Culicoides impunctatus (Diptera: Ceratopogonidae) in Scotland," Journal of the American Mosquito Control Association, 1996, pp. 329-330, vol. 12, No. 2, American Mosquito Control Association, Inc.

Trigg, J. K., "Evaluation of a Eucalyptus-Based Repellent Against *Anopheles* Spp. in Tanzania," Journal of the American Mosquito Control Association, 1996, pp. 243-246, vol. 12, No. 2, American Mosquito Control Association, Inc.

Trongtokit, Yuwadee, et al., "Efficacy of Repellent Products Against Caged and Free Flying *Anopheles stephensi* Mosquitoes," Southeast Asian J Trop Med Public Health, Nov. 2005, pp. 1423-1431, vol. 36, No. 6.

Tuetun, Benjawan, et al., "Repellent properties of celery, *Apium graveolens* L., compared with commercial repellents, against mosquitoes under laboratory and field conditions," Nov. 2005, pp. 1190-1198, vol. 10, No. 11, Blackwell Publishing Ltd.

Yang, Pin, et al., "Repellent effect of plant essential oils against Aedes aslopictus," Journal of Vector Ecology, Dec. 2005, pp. 231-234, vol. 30, No. 2.

Songkro, Sarunyoo, et al., "Effects of Glucam P-20, Vanillin, and Fixolide on Mosquito Repellency of Citronella Oil Lotions," Journal of Medical Entomology, Vector/Pathogen/Host Interaction, Transmission, 2012, pp. 672-677, vol. 49, No. 3, Entomological Society of America.

Nerio, Luz Stella, et al., "Repellent activity of essential oils: A review," Bioresource Technology, 2010, pp. 372-378, vol. 101, Elsevier Ltd.

\* cited by examiner

INSECT REPELLENT COMPOSITION AND METHOD OF USE

CROSS REFERENCE TO RELATED APPLICATIONS

This application is a continuation of and claims priority to PCT/GB2016/053430 filed Nov. 4, 2016 and entitled "Insect Repellent Composition and Method of Use," which claims priority to Great Britain Patent Application No. 1519781.7 filed Nov. 10, 2015 and Great Britain Patent Application No. 1617161.3 filed Oct. 10, 2016, which applications are incorporated by reference herein in their entirety.

BRIEF DESCRIPTION OF THE DRAWINGS

The following Figures illustrate the advantages of the present invention.

DETAILED DESCRIPTION

Figure 1:
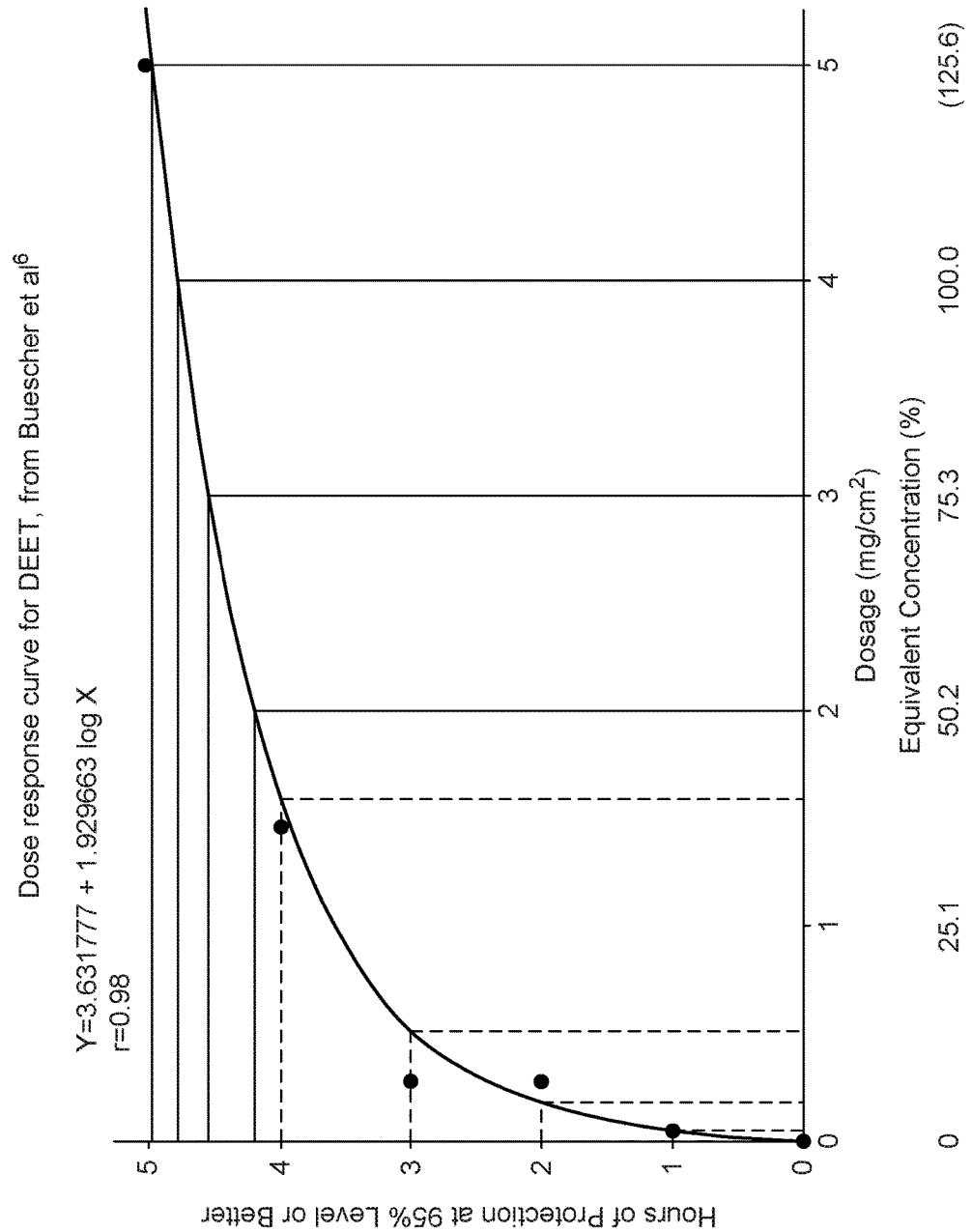
FIG. 1: Dose response curve for DEET, from Buescher et al[6].

The present invention is concerned with an insect repellent composition and a method of using the same to repel insects over an extended period of time. The compositions of the invention include natural insect repellents and can provide a prolongation of complete protection times to a 12 hour minimum thereby enabling a once daily dosage regime.

The compositions of the invention have particular utility in terms of repelling flies from the family Culicidae or Ceratopogonidae, especially mosquitoes and midges (collectively described herein as "biting flies"), where the repellent effect can be prolonged considerably compared to current standards and can last for 12 hours or more. The fundamental aim is to provide consumers with a unique, convenient once daily treatment, to improve patient compliance.

For a variety of factors, including a well understood and growing consumer chemophobia, there is an ever increasing demand from customers worldwide for insect repellents that are natural in origin and not based on synthetic chemical repellents, which have dominated the market in the last 70 years or more[1]. Hence, so-called "natural repellents" have grown rapidly in terms of usage during recent years and are now very often products of first choice in terms of consumer preference, particularly in countries such as the USA and UK.

However, of greater general health importance in terms of clinical mortality, certain mosquito species are well known vectors of serious diseases including the greatest "biters"/killers of children (malaria) and recent years have seen major increases in mortality associated with other serious diseases such as Dengue fever (notably in the Indian subcontinent), Yellow fever and West Nile virus.

For example, by 2015, Dengue fever had risen to epidemic proportions in some areas in the East (over 500,000 current cases in Mumbai, India alone) whilst to the West in the United States of America the more worrying trends have seen large documented increases in West Nile Virus and Lyme Disease.

Finally, in 2016 itself, the rapid emergence of the Zika virus, caused by the *Aedes Aegypti* mosquito vector, has had huge negative effects on healthcare in the major areas of South America, such as Brazil, resulting in the WHO confirming a state of emergency in such regions. The suspected link between the Zika virus and the rapid emergence of numerous cases of serious birth defects, e.g. microcephaly in children, is a frightening prospect in terms of its potential threat to "migrate" from South America to other regions of the world.

This is not a hypothetical threat as very recent events in Florida USA have demonstrated where locally bred *Aedes Aegypti* colonies have been found in the area and hence the discovery of Zika cases on the American mainland for the first time. This has led to an unprecedented warning from the Center for Disease Control (CDC) for pregnant women not to travel to a part of the United States, for the first time in its history.

Whilst the mosquito vector for malaria is the *Anopheles* species, the current vector for Dengue, Yellow fever and Zika is *Aedes Aegypti*, whilst the *Culex* mosquito vector is the cause of West Nile virus in the United States. Consequently, an effective modern mosquito repellent must offer a broad spectrum of species activity for prolonged periods of time.

The currently accepted first line of defence agreed by all healthcare/regulatory bodies aimed at disease prevention is more effective repellency. There is a need for compositions that show high levels of efficacy against at least these three species of mosquito vector and can offer protection for periods of hours consistently in excess of current standards e.g. up to and exceeding 12 hours per day. There is also a need for insect repellent compositions that could be used in a once daily dosing regime, and as such would be able to maintain sufficient insect repellency throughout an extended period of time, such as up to and exceeding 12 hours per day. Known insect repellent compositions would not be suitable for use in such once daily dosing regimes due to a lack of adequate repellency over extended periods of time. The current inventors have however surprisingly developed compositions that address the above needs and in particular enable effective once daily dosing whilst providing effective repellency over extended periods of time. The present invention thus clearly provides advantages compared to the prior art.

Whilst the experience of being exposed to the activities of biting flies is invariably an uncomfortable experience in many parts of Europe, where repellents are widely used for convenience purposes, the clinical need to maximise protection in the other world zones experiencing serious disease including Malaria, Dengue fever and Zika requires an urgent search for more effective repellents offering greater longevity of protection.

In terms of Dengue fever and the Zika virus, the *Aedes Aegypti* mosquito vector is unusually a "day biter", so the resulting requirement for 12 hours protection is an actual pre-requisite for an effective insect repellent for this species.

The testing of insect repellents has a well-established number of proven procedures in terms of regulatory acceptance and those other recommended tests by eminent bodies such as the WHO and the USA's Environmental Protection Agency (EPA). The two most favoured types of tests are those in a laboratory (the so-called "arm or hand in cage" tests) and those undertaken in the "open" natural environment (the so-called "field" tests).

Traditionally, in these tests, one of the most favoured parameters for the assessment of the ability of repellents (whether they be from natural or synthetic origin) to protect consumers/patients has been the measurement of protection times, particularly complete protection times (so-called CPTs). Repellents make humans unattractive to biting flies, such as a mosquito, so that the biting fly will avoid areas of the body that have been treated with the product. Repellents do not kill biting flies, such as mosquitoes. The best repellents will provide protection from bites for a long period of time from just one application. A well-recognized test to evaluate the effectiveness of such repellents is based on the amount of time the product will continue to repel biting flies, such as a mosquito, after one application to the skin.

Complete protection times are calculated as the number of minutes (or hours) elapsed between the time of repellent application and the first mosquito landing or probing. Complete Protection Times are reported herein as a median value of protection time given by each individual. Complete Protection Times are abbreviated herein as CPTs. The test employed to determine the same consisted of inserting a repellent (according to the present invention) treated arm into a cage measuring 35 cm on each side, containing laboratory bred 200 numbers of biting flies, such as non-blood fed *Aedes aegypti* mosquitoes that are 5-7 days old, and measuring the elapsed time to first landing or probing (which refers to an insect landing and penetrating the skin with its mouthparts, without ingesting blood).

In the main and to date, CPTs have ranged from 2 hours to 6 hours for the major marketed repellents such as the leading chemical repellent, DEET [N,N-Diethyl-3-methyl-benzamide], or the leading natural repellent, p-menthane-3,8-diol, known in the USA as Oil of Lemon *Eucalyptus* (OLE), or as PMD in the European Union (currently available under the trade marks "Citriodiol" and/or "Citrepel"].[1][2]

The market dominant synthetic product, DEET as referred to above, has been used in relatively high concentrations of between 50-100% and a limited number of DEET containing formulations have claimed CPTs of over 6 hours[2] in some communications. In fact, there is on the Australian market a DEET gel marketed by Bushman containing an 80% concentration of DEET.

Whilst these ranges of CPTs were/are reasonably or potentially acceptable for so-called "cosmetic purposes", there have been increasing recent trends in numerous parts of the world of unacceptably high rates of illness and/or mortality associated with the well-recognised diseases caused by mosquito vectors, such as Malaria, and more recently other life-threatening diseases.

The very recent post 2010 outbreaks of diseases such as Dengue fever, Yellow fever, and now the Zika virus have added to the ever present problem of disease control and have created a much more urgent need for repellents demonstrating added levels of protection with CPTs allowing 12 hour efficacy (or even more, i.e. protection well in excess of the traditional level of satisfactory protection).

Attempts to intervene with well-known pharmaceutical formulation techniques to extend the "conventional" protection times are not new or revolutionary and indeed they have predominantly concentrated upon the leading chemical repellent, DEET, in a number of previous studies.[3][4]

DEET was developed for the American military forces for use during and after World War II and was eventually released on to world markets as an insect repellent in circa 1957. Since then it is estimated that over 8 billion applications of the various DEET-containing products have been administered.[4]

In terms of the CPT profile for DEET, with reference to the pivotal US military study from Buescher et al.[6], 1983, its dose response confirms that its activity plateaus at around 5-6 hours at circa 50% concentrations, as demonstrated in FIG. 1.

This was presumably the rationale for attempts to improve DEET's CPT profile beyond 6 hours whilst not increasing its concentration in marketed formulations. Although DEET has an accepted positive benefit/risk ratio, a number of leading regulatory health authorities have become increasingly concerned regarding its toxicity and its proven systemic absorption—an unusual characteristic in contrast with most other repellents. Some authorities have suggested an upper DEET concentration of 20% (Europe) or 30% (Canada). A recent independent review by Goodyear et al. confirmed that a 30% limit would be a prudent top concentration[5].

Figure 2:
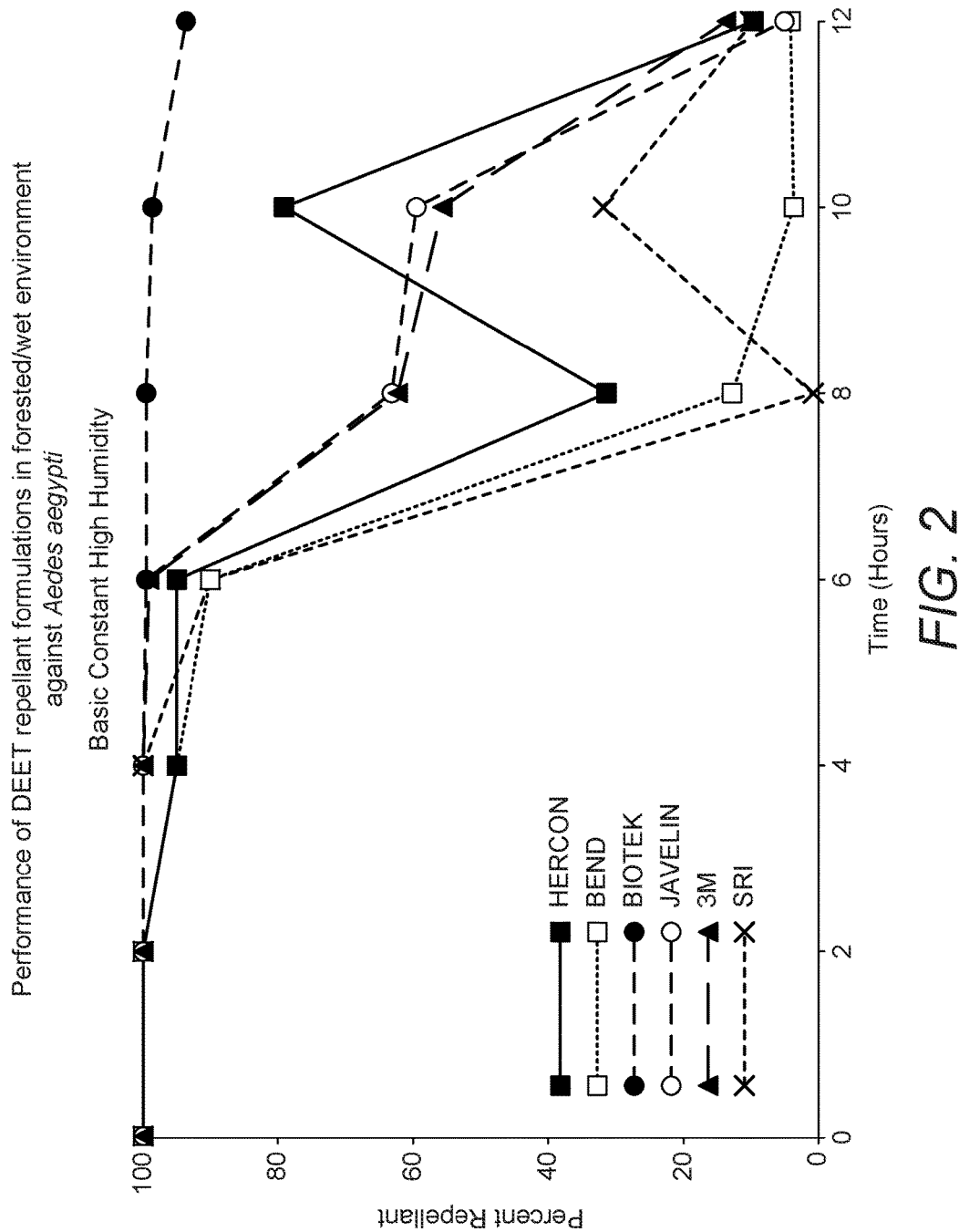
FIG. 2: Performance of DEET repellent formulations in forested/wet environment against *Aedes Aegypti*.
Figure 3:
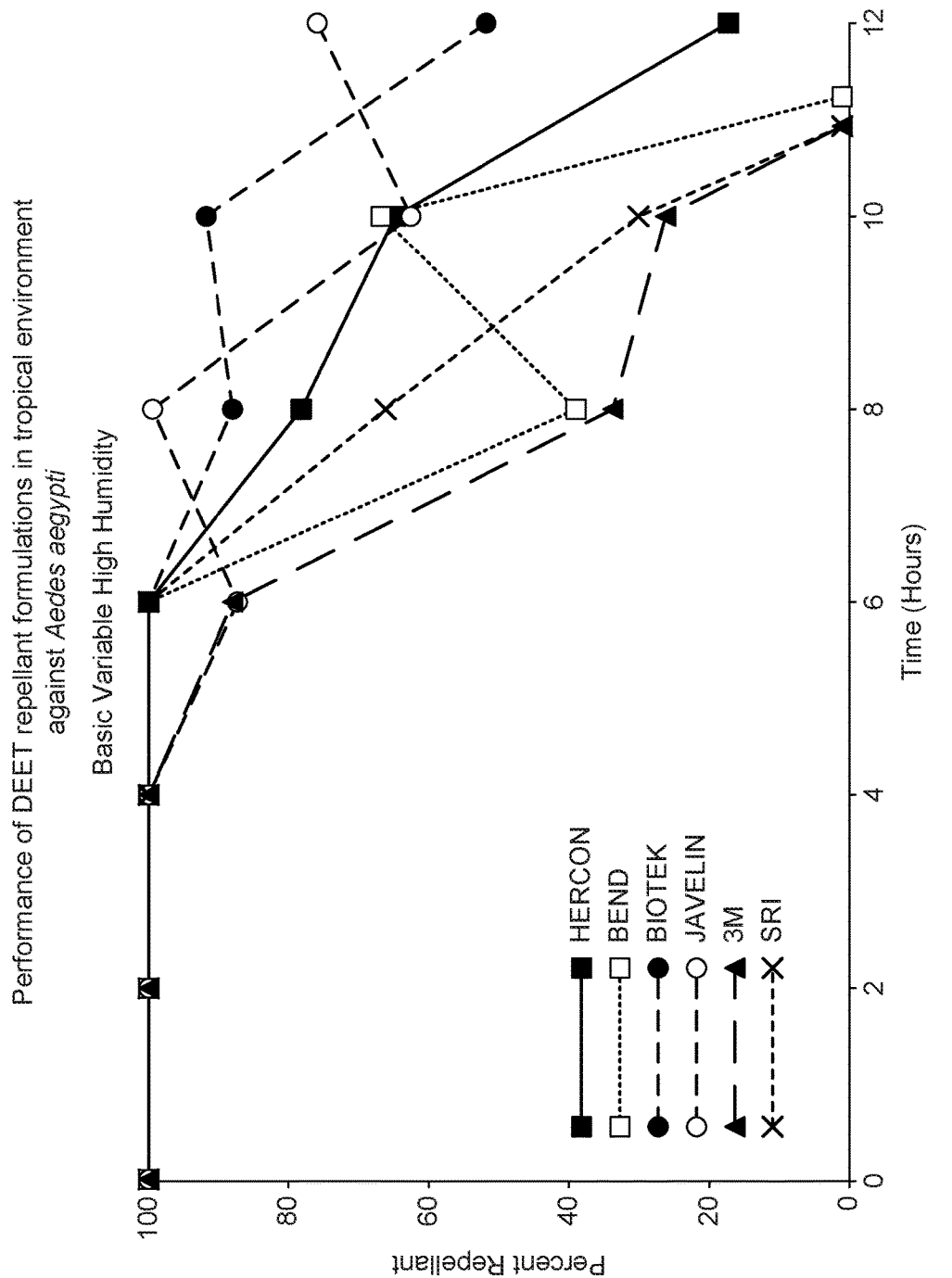
FIG. 3: Performance of DEET repellent formulations in tropical environment against *Aedes Aegypti*.
Figure 4:
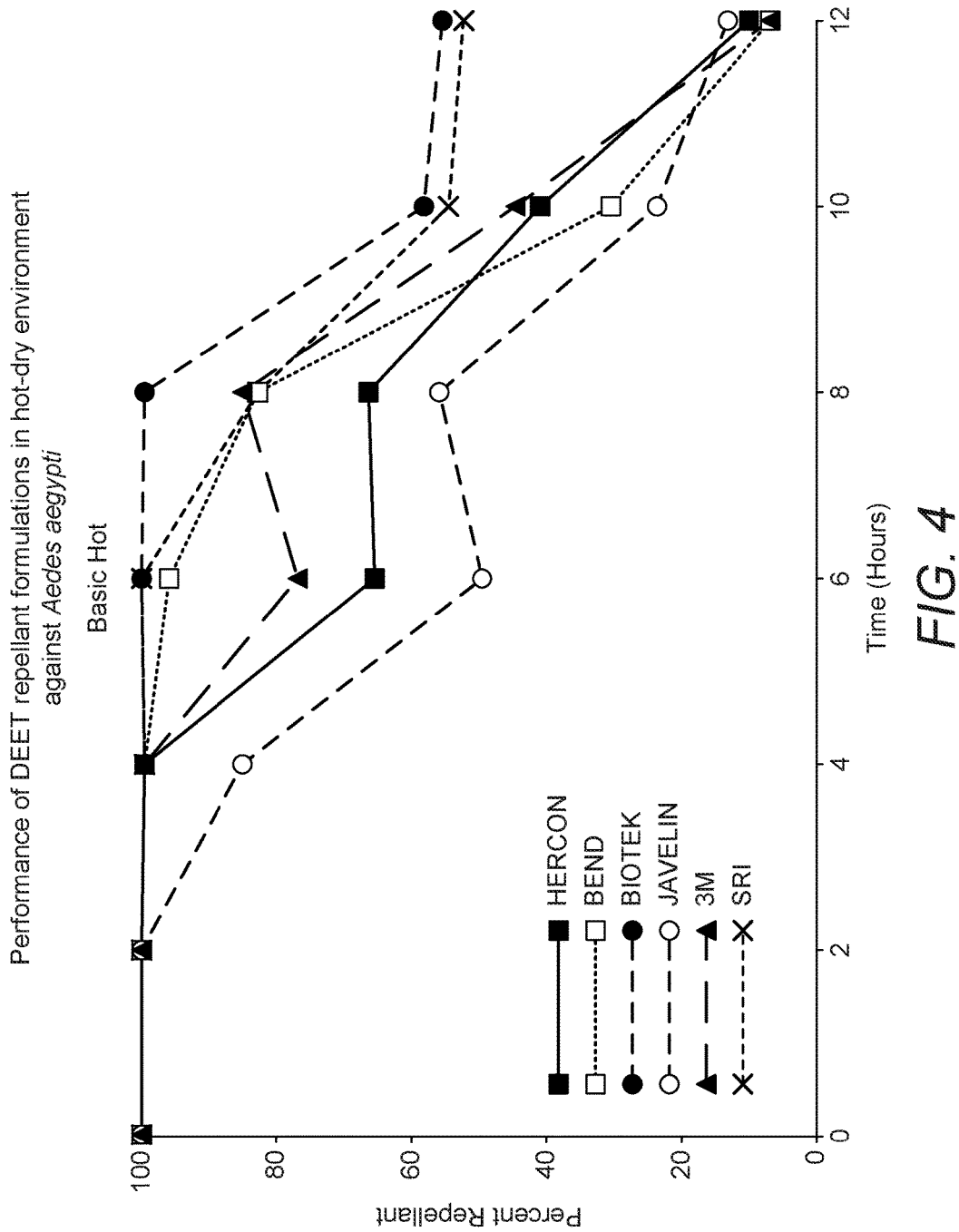
FIG. 4: Performance of DEET repellent formulations in hot-dry environment against *Aedes Aegypti*.

In the previous pivotal study by Gupta et al.[3], a number of extended release technologies (up to 6 in fact) were evaluated in comparative terms with DEET and the resulting CPTs were extended from about 2 to 4 hours to over 6 hours in some cases (subject to test conditions)—a positive improvement but hardly striking, as demonstrated in FIGS. 2, 3, and 4.

It is clear that the observed levels of increase in protection were not very pronounced and fell very short of the optimum 12 hour minimum target required in the current era. Such extended protection times are clearly not an easy task to achieve.

Following the unprecedented success levels of the DEET synthetic chemical repellent, other researchers have developed more recent chemical repellents, such as ethyl butylacetylaminopropionate (IR3535) and Picaridin (KBR 3023). A more detailed comparison of these synthetic repellents is given in the papers from Goodyear[2] and Maia[8].

However, neither ethyl butylacetylaminopropionate (IR3535) nor Picaridin (KBR 3023) has demonstrated meaningful superiority to DEET in terms of CPTs.

In this context, it has been previously postulated that the repellent effect (CPT) of some synthetic and natural insect repellents (for example N,N-Diethyl-3-methylbenzamide (DEET), ethyl hexanediol, dimethyl phthalate, butyl 3,4- dihydro-2,2-dimethyl 4-oxo-2H-pyran-6-carboxylate (available under the trade mark Indalone), triethylene glycol monohexyl ether, triethylene glycol monoheptyl ether and triethylene glycol-2-ethylhexyl ether) can be prolonged by mixing the repellent with vanillin (4-hydroxy-3-methoxybenzaldehyde) and applying that mixture to a user (see Kahn et al. "Addition Of Vanillin To Mosquito Repellents To Increase Protection Time" Mosquito News June 1975).

It may be seen from that paper that the prolongation was achieved by the use of substantial quantities of vanillin (one half, equal or two to three times the quantity of repellent) were used. The addition of vanillin did not, however, greatly improve the CPTs, and certainly did not provide CPTs long enough to provide a user protection for an entire night, for example, or for a period of 10 to 12 hours after a single application of the treatment at the start of the day, or indeed, the entire day from morning to evening in terms of the necessary protection against the specific day-biter, *Aedes Aegypti*.

One obvious disadvantage of these high concentrations of vanillin would undoubtedly be the smell of the finished formulation due to the rather overwhelming smell of vanillin, which is experienced even at low/medium concentrations.

Finally, with respect to DEET and also synthetic repellents more generally, the use of synthetic repellents such as DEET has several drawbacks including potential health risks and concerns, especially to children, since DEET is absorbed through human skin. In addition, the odour of DEET is considered by many to be "chemical" and unpleasant and it can sting when applied to the skin. Hence, a suitable consumer friendly repellent formulation is needed.

In view of the potential drawbacks associated with DEET, there has been a market and developmental trend for the introduction of "natural repellents" with the most significant advancement being the acceptance of the first natural repellent by the US Center for Disease Control and Prevention (CDC) in 2005, namely p-menthane-3,8-diol (also known as "PMD" in many countries worldwide, but "OLE", Oil of Lemon *Eucalyptus*, in the USA). Its positive history and results from new laboratory and field tests have been summarised eloquently in the pivotal Carroll paper.[9]

Therefore, in recent years, a number of the developed international markets for insect repellents have consistently shown trends away from synthetic chemical repellent products such as DEET. An ever increasing acceptance has developed for potential natural solutions, with their accepted improvements in tolerance and advantages in terms of reduced toxicity and wider patient acceptability.

A particularly preferred "natural" terpenoid is the aforementioned p-menthane-3,8-diol (also known as PMD/Oil of Lemon *Eucalyptus*), which has been launched successfully in the UK in the 1990s, prior to its CDC approval in the US in 2015.

"Citriodiol" (trade mark) was the first p-menthane-3,8-diol (PMD)-based insect repellent active ingredient to be introduced to the European market, as the active ingredient in the end use product brand available under the trade mark "Mosi-guard" in 1995, when it came onto the market in the UK. Its superior efficacy in comparison to other naturally sourced insect repellents had been known for many years prior to this in China, (where it was known as "Quwenling"—"effective mosquito repellent") and its use there led to it being brought to the market in Europe. Its superiority as a natural repellent was recognised in a number of pivotal studies undertaken by Hill[6], Moore[10], Trigg[14] etc., a number of leading investigators/researchers at the world renowned London School of Hygiene and Tropical Medicine (see list of references). As well as the product available under the trade mark "Mosi-guard" having been sold in the UK for over 20 years, a corresponding product has been available in other leading EU markets such as Spain and France since approximately 2000.

The product available under the trade mark "Citriodiol" from Citrefine International has also been used as an active ingredient in other consumer brands for many years, appearing first in Sweden and then in a host of other countries including Denmark, Germany, Italy, Greece and Hungary. "Citriodiol" is now also used in repellents for use on horses, cats and dogs and as a head louse repellent. Its use in these and more traditional dermally applied repellents for humans is now widespread within Europe and across the globe.

Despite a wide range of anecdotal and unjustified claims for various other natural products from different regions of the world, it is critical to note a number of finished products containing these so-called actives have not been supported by credible clinical and scientific evidence, including such products as Citronella, Lemon Grass, etc.[1,2,8]

During its period of well-established usage from the 1990s onwards, varying lengths of CPT were observed with PMD in numerous studies[6,9,10,11,12,13,14] ranging from 4 to 6 hours in the main. Consequently, with previous formulations one application had to be repeated on more than one occasion if CPTs of 12 hours or more were to be achieved leading to a likely negative compliance with most consumers/patients. Ease of usage and the clearly linked benefits in improved patient compliance is a key target in the development of modern medicines and treatments with once daily dosage being the optimum development target.

One of the accepted physiochemical properties demonstrated by this type of natural oil is a high level of volatility associated with rapid evaporation and hence the major challenge of increasing CPTs in excess of 6 hours up to and exceeding 12 hours is particularly difficult in this group of interesting natural compounds.

Figure 5:
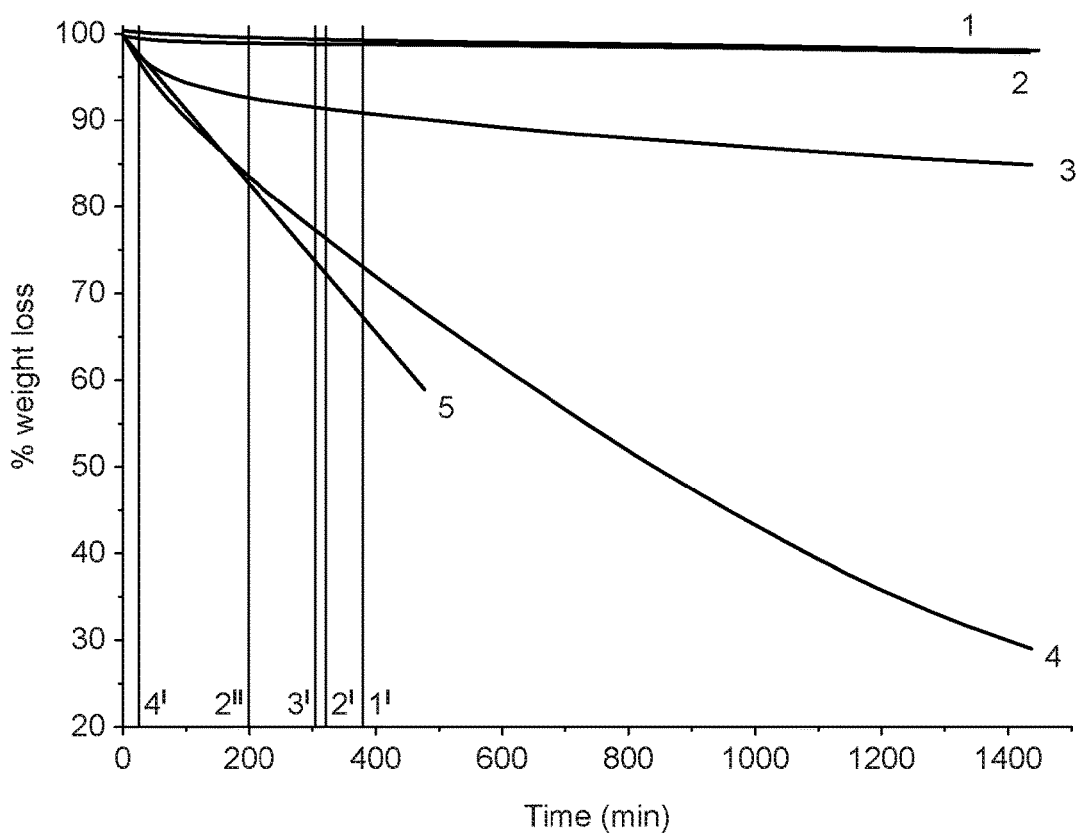
FIG. 5: TGA curves of the evaporation rate of DEET (1), PMD (2), modified *Eucalyptus citriodora* oil (3), *E. citriodora* oil (4) and pure (+) citronellal (5).

The inventors noted that PMD has the lowest observed volatility of this group of natural products and in fact has been shown to be similar to DEET, in terms of profile, as shown in FIG. 5. If one focuses on line 1 (DEET) and line 2 (PMD), the similarities in observed volatility can be easily seen.

In developing the compositions of the present invention, the inventors selected PMD as a natural oil to be used in their compositions. This unusual property of PMD, compared to other essential oils, was thus an important factor in its use as a natural repellent of choice in the compositions of the present invention.

As stated previously, the toxicity of DEET has been the subject of a number of reviews due to its potential health risks and consumer concerns, particularly in the context of its unusual system absorption through the human skin. Moreover, although the product has an acceptable benefit/risk ratio balanced review, many consumers dislike its "chemical odour" and its frequent stinging sensation when applied to the skin.

Moreover, numerous field studies, undertaken in various continents, have confirmed less protection against species such as *Anopheles*, the malaria vector species, as stated in the pivotal Goodyear paper[2]:

"The response of different mosquito species to DEET is variable.[17] Field tests of repellent formulations containing DEET against biting *Culex* spp., *Aedes* spp., *Mansonia* spp., and *Verrallina* spp. have been reported.[5]

The protection provided by DEET was longer against these genera than provided against *Anopheles* spp."

It is concerns of this type that have been a motivation for other researchers to investigate further the possible role of natural repellents due to the ever increasing consumer cynicism/restrictions of this type with synthetic repellents. Furthermore, the present inventors have found that the natural oil PMD can achieve the minimum CPT target for 12 hours.

Hence, the basic development challenge that faced the inventors was how to employ innovative prolonged-release pharmaceutical methods to extend the protection offered by a natural insect repellent, such as PMD. There was also a need for this to be used as a monotherapy terpenoid, and to incorporate this active substance in a prolonged action formulation. The aim of the inventors was to provide natural formulations offering CPTs of 12 hours or more. This extra gain of 6 hours, or more, clearly represented a very significant "quantum leap" in the CPTs offered by known products.

One of the most promising avenues of relevant research followed by the inventors has concentrated upon the possible combinations of PMD with other molecules comprising aldehyde functional groups that can form compounds such as acetals, reversibly. While not being bound by theory, the inventors have postulated that these PMD-acetals, which are less volatile than PMD, can be administered in dermal formulations, whereby the acetals are broken down to the constituent PMD and aldehyde at a slow release rate, thereby prolonging the repellent protection of the active PMD. The following reaction scheme is postulated by the inventors based on the reversible formation of PMD-acetals from PMD and aldehydes.

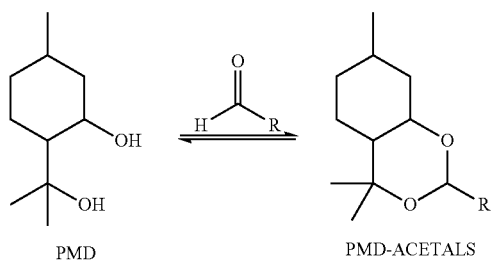

PMD    PMD-ACETALS

R = alkyl, aryl, hetero aryl

The molecule, vanillin was previously investigated by the DEET researchers and appeared to show limited potential as a fixative. From these DEET studies, there was therefore no incentive in the prior art to use vanillin as a fixative in an insect repellent composition due to the limited efficacy that was demonstrated for vanillin as a fixative. In view of the advantageous CPTs as achieved by the formulations of the present invention which include vanillin, the inventors believe that vanillin may have the appropriate type of chemical structure to combine effectively with PMD, unlike DEET, as shown below. There was no suggestion in the prior art of the CPTs that the inventors have now achieved for a PMD insect repellent composition.

Molecular Structure of Vanillin

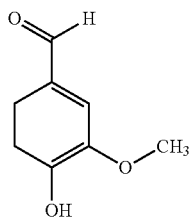

Molecular Structure of PMD

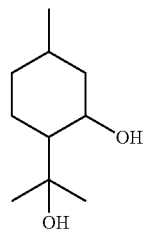

Molecular Structure of DEET

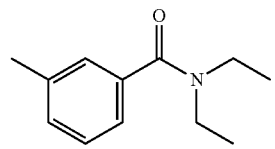

Clearly, the molecular structure of DEET is considerably different to that of vanillin and PMD, as shown above.

Vanillin has also used as a fixative in the combination with two terpenoids in U.S. Pat. No. 7,846,464 B2 (Darling) at lower concentrations. However, in the patent the actual extent of the observed protection produced by the addition of the second active compound, Lemon Grass, as the fixative itself, was not recorded and, of course, the "protection times" observed were only of the order of 4-6 hours. Such protection times are considerably lower than the target of 12 hours in this development programme, and as such a person skilled in the art would not have been inclined to follow the teaching in U.S. Pat. No. 7,846,464 B2 when looking to develop a composition that would be capable of providing the target CPTs of 12 or more hours.

A further important consideration for a skilled reader of U.S. Pat. No. 7,846,464 B2, would have been that in Europe and the USA itself, Lemon Grass is not an approved natural insect repellent (see Article 95 of the Biocide Regulation). In fact, only "Citriodiol" (PMD) is approved at the time of writing. Thus PMD combination products, such as described in U.S. Pat. No. 7,846,464 B2, would not be possible insect repellent compositions in practice, since they would be ruled out on regulatory grounds alone. Moreover, Lemon Grass is not an EPA approved insect repellent in the USA and its effectiveness as an insect repellent has been demonstrated to be of a lower order of magnitude in other studies.[8]

The present inventors have now found clear advantages associated with the use of vanillin in the compositions of the present invention. These advantages include an appropriate chemical structure to allow acetal formation as above, a good dermatological sensitisation record, excellent general safety/toxicity record (GRAS substance in the USA) and good tolerability as an excipient with EU and US Regulators. Prior to the present invention however, the advantages provided by the present invention could not have been predicted and indeed a skilled reader of the prior art would have been disinclined to use vanillin in a composition according to the present invention. More specifically, the skilled reader would have been aware of the following potentially negative properties that are associated with vanillin—its electron-rich aldehyde structure could render it less reactive to acetal formation and as such not ideal for use as a fixative in a composition require g extended CPTs, its well documented record of instability, its photosensitivity (sunlight degradation c.5 hours), its tendency to oxidise in water—abiotic degradation, the generally expected requirement for high concentrations and its overpowering smell—unacceptable to some consumers.

In contrast to the formulations disclosed in U.S. Pat. No. 7,846,464 B2, the objective of this innovation was to offer monotherapy in terms of a terpenoid at medium concentrations of PMD with a "quantum leap" of some proportion (circa 6 hours) up to 12 hours as a minimum CPT. The present invention as will be described in further detail hereinafter thus addresses shortcomings that were associated with known prior art regimens.

According to the present invention, there is now provided a composition and method of use as set out in the following statements of invention and claims as appended hereto.

Statements of Invention

1. An insect repellent composition comprising p-methane-3,8-diol, vanillin, an antioxidant that prevents discoloration of said vanillin when said composition is stored at 54° C. for 14 days and a delivery vehicle.

2. An insect repellent composition comprising p-methane-3,8-diol as the sole insect repellent, vanillin and a delivery vehicle.

3. An insect repellent composition comprising p-methane-3,8-diol, vanillin and a delivery vehicle, wherein said insect repellent composition provides a complete protection time of at least 8 hours.

4. An insect repellent composition comprising p-methane-3,8-diol, vanillin and a delivery vehicle, for once or bi-daily administration.

5. An insect repellent composition comprising p-methane-3,8-diol, vanillin and a delivery vehicle, for prevention of the Zika virus.

6. An insect repellent composition comprising p-methane-3,8-diol, vanillin and a delivery vehicle, for repelling the Scottish Highland midge (Meanbh-chuileag).

7. An insect repellent composition comprising p-methane-3,8-diol, vanillin and a delivery vehicle, for the prevention of a disease state caused by the *Culex* mosquito.

8. An insect repellent composition according to any of statements 2 to 7, which further comprises an antioxidant that prevents discoloration of said vanillin when said composition is stored at 54° C. for 14 days.

9. An insect repellent composition according to statements 1 or 8, wherein said antioxidant comprises sodium bisulphite.

10. An insect repellent composition according to statement 9, wherein said sodium bisulphite is present in an amount of about 0.5 to about 1.5% weight % of the composition.

11. An insect repellent composition according to any of statements 1, or 3 to 7, wherein p-methane-3,8-diol is present as the sole insect repellent.

12. An insect repellent composition according to any of statements 1, 2 or 4 to 7, wherein said composition provides a complete protection time of at least 8 hours.

13. An insect repellent composition according to statement 3 or 12, wherein said composition provides a complete protection time of at least 10 hours 14. An insect repellent composition according to statement 13, wherein said composition provides a complete protection time of at least 12 hours.

15. An insect repellent composition according to statements 1 to 3, or 5 or 7, for once or bi-daily administration.

16. An insect repellent composition according to any of statements 1 to 4, for the prevention of a disease state that is caused by *Aedes Aegypti*.

17. An insect repellent composition according to statement 16, wherein said disease state is selected from Dengue fever, Yellow fever and the Zika virus.

18. An insect repellent composition according to any of statements 1 to 4, for repelling the Scottish Highland midge (Meanbh-chuileag).

19. An insect repellent composition according to any of statements 1 to 4, for the prevention of a disease state that is caused by the *Culex* mosquito.

20. An insect repellent composition according to statement 19, wherein said disease state is the West Nile virus.

21. An insect repellent composition according to any preceding statement, wherein said vanillin is present in an amount of about 5 to 15% by weight of said composition, more typically at least about 10% by weight of said composition.

22. An insect repellent composition according to any preceding statement, which said p-methane-3,8-diol is present in an amount of at least 10% by weight of said composition.

23. An insect repellent composition according to any preceding statement, which said p-methane-3,8-diol is present in an amount of at least 12% by weight of said composition.

24. An insect repellent composition according to any preceding statement, which said p-methane-3,8-diol is present in an amount of at least 15% by weight of said composition.

25. An insect repellent composition according to any preceding statement, which said p-methane-3,8-diol is present in an amount of at least 18% by weight of said composition.

26. An insect repellent composition according to any preceding statement, which said p-methane-3,8-diol is present in an amount of at least 20% by weight of said composition.

27. An insect repellent composition according to any preceding statement, which said p-methane-3,8-diol is present in an amount of at least 25% by weight of said composition.

28. An insect repellent composition according to any preceding statement, which said p-methane-3,8-diol is present in an amount of at least 30% by weight of said composition.

29. An insect repellent composition according to any preceding statement, which said p-methane-3,8-diol is provided by a source of p-methane-3,8-diol that is commercially available under the trade mark "Citriodiol".

30. An insect repellent composition according to statement 29, wherein said "Citriodiol" is present in an amount of about 20 to 50% by weight of said composition.

31. An insect repellent composition according to statement 29, wherein said "Citriodiol" is present in an amount of about 25 to 50% by weight of said composition.

32. An insect repellent composition according to statement 29, wherein said "Citriodiol" is present in an amount of about 25 to 35% by weight of said composition.

33. An insect repellent composition according to statement 29, wherein said "Citriodiol" is present in an amount of about 30% by weight of said composition.

34. An insect repellent composition according to statement 33, that provides p-methane-3,8-diol in an amount of about 18 to 20% by weight of said composition.

35. An insect repellent composition according to statement 29, wherein said "Citriodiol" is present in an amount of about 40 to 50% by weight of said composition.

36. An insect repellent composition according to statement 35, that provides p-methane-3,8-diol in an amount of about 24 to 34% by weight of said composition.

37. An insect repellent composition according to any of statements 1 to 28, which said p-methane-3,8-diol is provided by a source of p-methane-3,8-diol that is commercially available under the trade mark "Citrepel".

38. An insect repellent composition according to statement 37, that provides p-methane-3,8-diol in an amount of about 30 to 40% by weight of said composition.

39. An insect repellent composition according to any preceding statement, wherein said delivery vehicle is an aqueous delivery vehicle.

40. An insect repellent composition according to any preceding statement, wherein said delivery vehicle comprises water and at least one alcohol.

41. An insect repellent composition according to statement 40, wherein said alcohol comprises isopropyl alcohol.

42. An insect repellent composition that comprises p-methane-3,8-diol, vanillin, sodium bisulfite, water and isopropyl alcohol.

43. An insect repellent composition according to statement 42, wherein said p-methane-3,8-diol is provided by a source of p-methane-3,8-diol that is commercially available under the trade mark "Citriodiol".

44. An insect repellent composition according to statement 43, wherein said "Citriodiol" is present in an amount of about 40% by weight of said composition.

45. An insect repellent composition according to statement 42, wherein said vanillin is present in an amount of about 10% by weight of said composition.

46. An insect repellent composition according to statement 42, wherein said sodium bisulfite is present in an amount of about 1% by weight of said composition.

47. An insect repellent composition according to statement 42, wherein said isopropyl alcohol is present in an amount of about 40% by weight of said composition.

48. An insect repellent composition according to any of the preceding statements, which is a spray, lotion, gel or roll-on.

49. A container containing a composition according to statement 48.

50. An article of manufacture, such as a mosquito net or a dermal wipe, that is impregnated with a composition according to any of statements 1 to 48.

51. A method of preventing a disease state caused by a biting fly, or repelling a biting fly, which method comprises administering to the skin of a user a composition according to any of statements 1 to 48.

52. A method according to statement 51, for the prevention of a disease state that is caused by *Aedes Aegypti*.

53. A method according to statement 52, wherein said disease state is selected from Dengue fever, Yellow fever and the Zika virus.

54. A method according to statement 51, for repelling the Scottish Highland midge (Meanbh-chuileag).

55. A method according to statement 51, for the prevention of a disease state that is caused by the *Culex* mosquito.

56. A method according to statement 55, wherein said disease state is the West Nile virus.

EXAMPLES

The present invention will now be further illustrated by the following examples that do not limit the scope of the invention in any way.
Experimental Protocol The first set of experiments involved a full investigation of the dose response of PMD itself at low, medium and high concentrations to ascertain whether PMD on its own could achieve the target protection times. Other studies had investigated the various doses of PMD but not in a controlled, scientific dose response study, as planned in the following experiments.

In addition to the new dose response study, the inclusion of low to medium concentrations of the first fixative, vanillin' in this instance, up to c.15% were planned for investigation.

The type of investigation test selected was the laboratory arm or hand in cage test and the first mosquito species selected was *Aedes Aegypti*. The tests were undertaken to WHO standards, as described in the following sections with the basic methods summarised below:—

| | |
|---|---|
| Test species | *Aedes aegypti* female mosquitoes, 5-7 days old, fed with sugar, no blood meal before test, Starved for 12 hours before the test |
| Number of mosquitoes per cage | 200 females |
| Test area | Wrist to elbow |
| Area of treated surface | Average of circumference at wrist, elbow multiplied by distance from wrist to elbow |
| Reporting of results | Duration of repellent protection until the time of first bite for each test subject |
| Treated Hand exposure | 5 minutes |
| Untreated hand exposure | 30 seconds |

The experiments were undertaken at the highly experienced, international centre of excellence, Ross Lifesciences, Pune, Maharashtra, India.

Example 1—Dose Response Study of Monotherapy (PMD Active—"Citrepel 75"); Effects of Fixative (Low/Medium Vanillin Concentrations)

Figure 6:
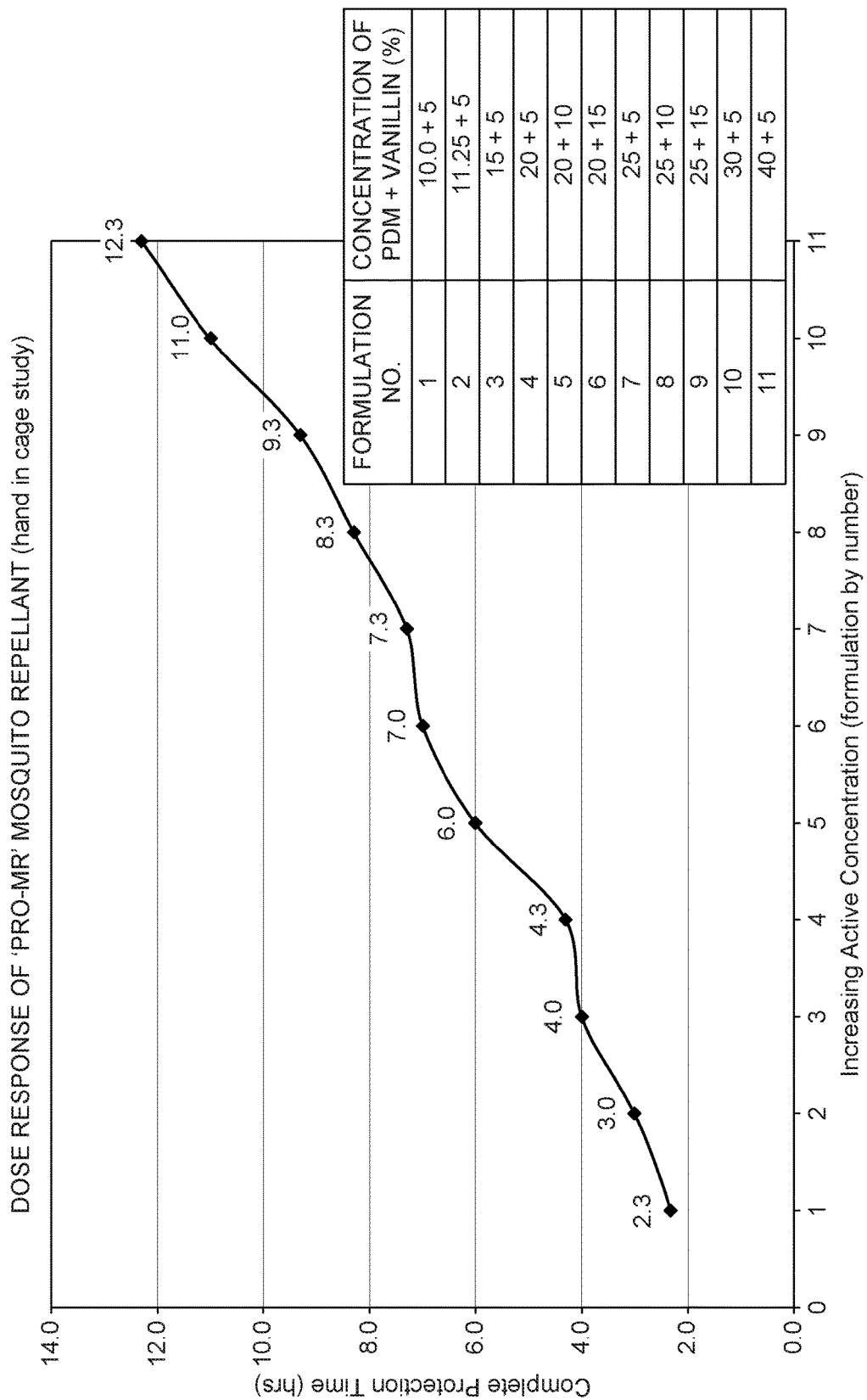
FIG. 6: Dose response curve of a mosquito repellent with varying % s PMD/vanillin.
Figure 7:
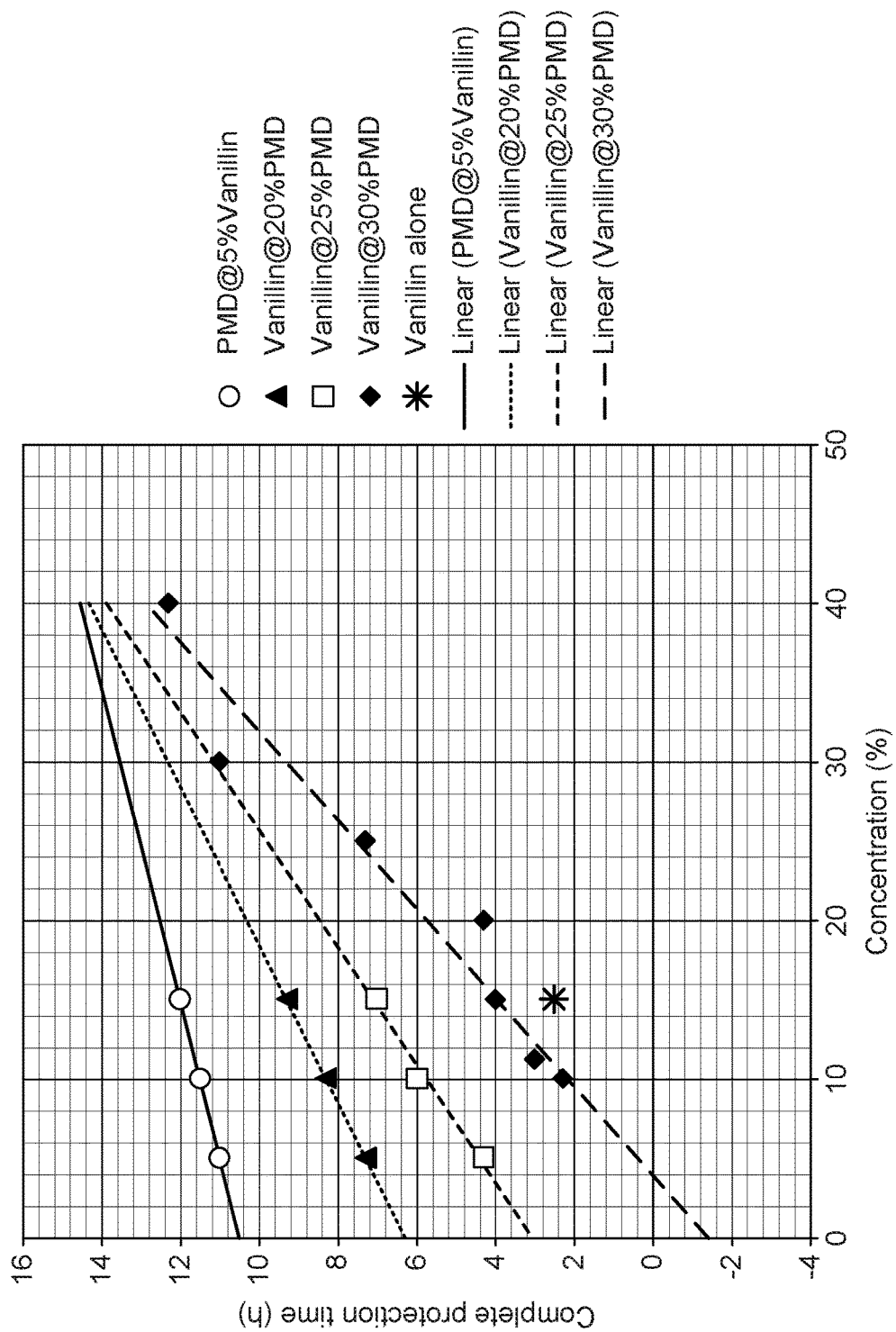
FIG. 7: Dose response curve of a mosquito repellent with varying % s PMD/vanillin.

Experiments with PMD concentrations ranging from 10-50%, with at least 10% intervals were planned and then specific concentrations ranging from 20%, 25% and 30% were combined with 3 individual concentrations of the fixative, vanillin. A summary of the results is given in FIGS. 6 and 7.

In these experiments a number of negative controls (e.g. vanillin itself) or positive controls (DEET and some others) were also investigated.

It can be observed that CPTs of 12 hours were optimally achieved with concentrations of PMD of 30-40% and vanillin concentrations ranging from 5-15%.

Therefore, the results of using medium concentrations of PMD alone, as monotherapy, in addition to low/medium concentrations of vanillin as the fixative, provided the surprisingly successful target result of CPTs of 12 hours as a minimum. The results were achieved without the expected and planned inclusion of additional fixatives.

It should be noted that due to the ethics control of the study, the protocol did not allow or envisage testing of volunteers above 12 hours so some planned tests were curtailed at 40% PMD, and 15% vanillin, for ethical reasons. The data would suggest that increased CPTs above 12 hours were capable of being attained at higher concentrations of PMD and/or vanillin, although certain planned studies at 40% and 50% were not completed for these described ethical considerations.

The very surprising large increase in CPTs observed is indicative of a possible unexpected synergy between PMD and vanillin.

A simple but reliable method of evaluating interactions in the PMD/vanillin combination experiments is to calculate the so-called coefficient of drug interaction (CDI). This calculation will establish if the substances are interacting, in one of these possible ways:—
a) additive; b) antagonistic; c) synergistic.

CDI is calculated as shown below:
CDI=AB/A×B—where AB is the result for the combined product and A and B are the separate results for the individual components.

If CDI is <1 this shows synergy. If <0.7 shows this significant synergy

If CDI=1, then the effect is additive

If CDI>1 then this shows antagonism.

So, for 20% PMD with 15% vanillin, experimental data show protection for 7 h.

So, CDI=7/(2.5×3.07)=0.912. This indicates synergism (weak) since CDI<1.

For 25% PMD with 15% vanillin, experimental data shows protection for 9.3 h.

So, CDI=9.3/(2.5×6.3)=0.6. This indicates significant synergy since CDI<0.7.

Due to the truncations of the test, PMD 30%/vanillin 15% was not undertaken due to the limitations of the test for ethical reasons.

Example 2—Comparison of Optimum Concentration Formulations to International Brands (India, UK, USA)

Figure 8:
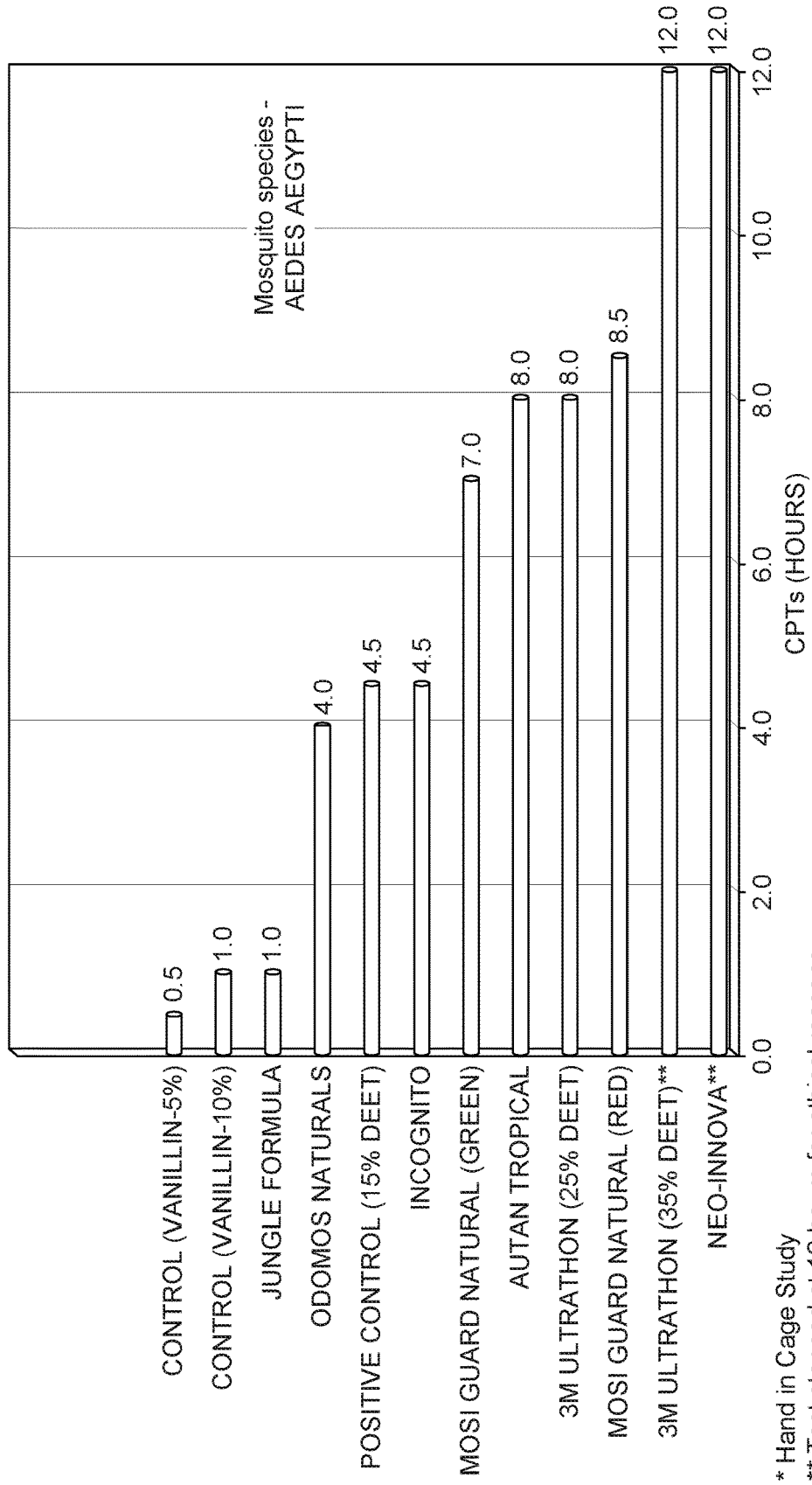
FIG. 8: Comparison of PMD (30%)/vanillin (10%) formulated in a hydroalcoholic solution to numerous well-known leading UK and US brands.

A second set of laboratory Hand in Cage experiments was undertaken in order to compare the chosen "optimised combination" of PMD (30%)/vanillin (10%) formulated in a hydroalcoholic solution to numerous well-known leading UK and US brands, as shown in FIG. 8.

It can be seen that the test solution (NEO-INNOVA) is superior in terms of observed CPTs to all the various leading international natural and synthetic brands with the exception of one, a high concentration prolonged release DEET formulation where equivalence was demonstrated. However, as already discussed, DEET has its own drawbacks and there is increased desire to use natural insect repellents as hereinbefore described.

The CPT of the positive control (DEET 15%) was 4.5 hours.

Example 3—PMD Dose Response for "Citriodiol" Active Substance (Low Concentrations of PMD)

Figure 9:
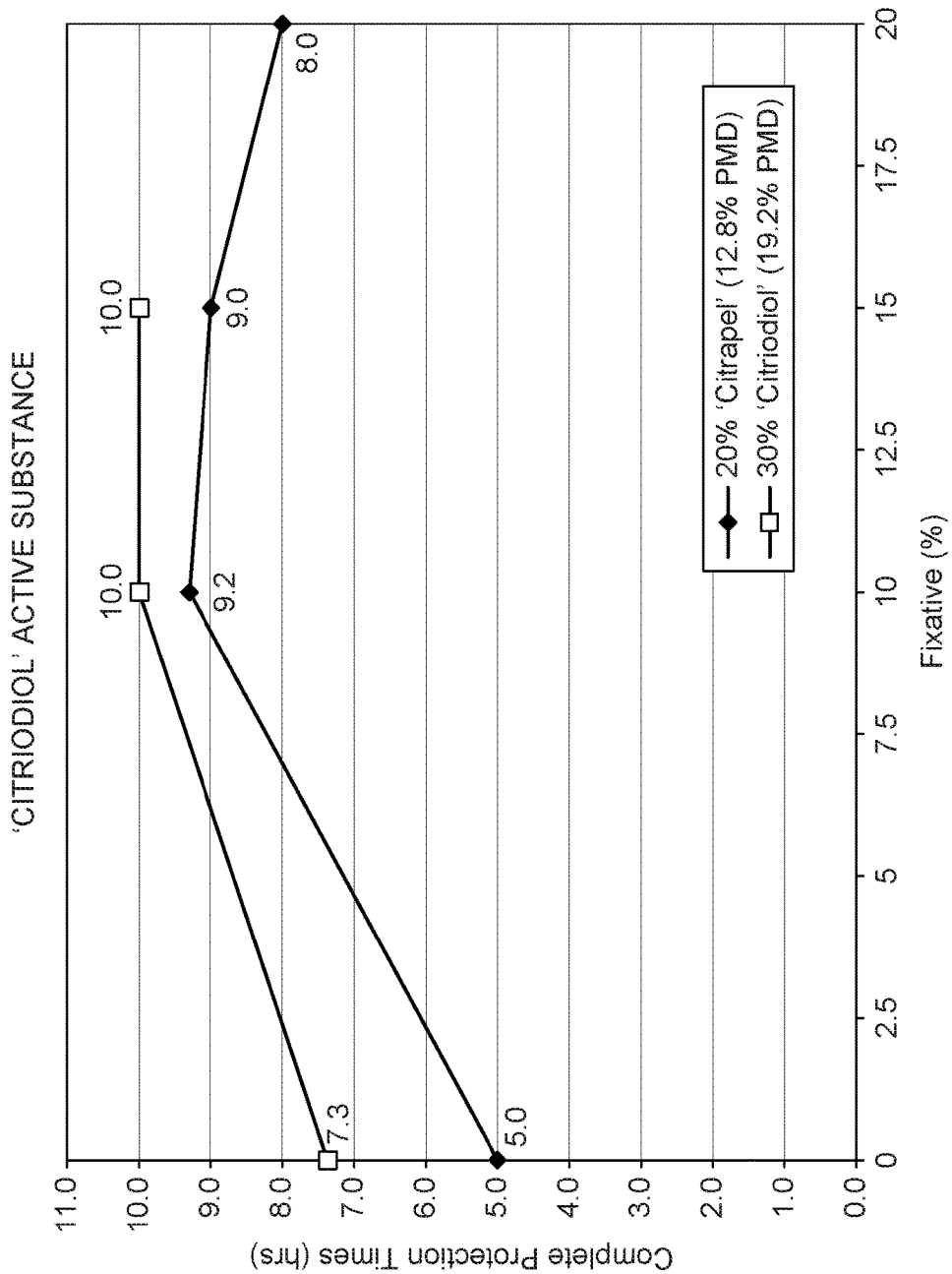
FIG. 9: CPTs with 20% "Citrepel" and 30% "Citriodiol" and different % amounts vanillin.

The third set of experiments demonstrated the results given below for lower concentrations of PMD than the previous tests with the "second" active substance "Citriodiol", approved in the UK and USA, and supplied by the company Citrefine International Limited. The results are shown in FIG. 9.

The success of the vanillin fixative was clearly confirmed at the lower marketed "Citrepel"/"Citriodiol" concentrations of 20%-30%, equivalent to 12.8% and 19.2% of PMD itself, from the concentrate mix.

When the different active substances utilised "Citrepel 75" and "Citriodiol" were compared in terms of observed CPTs, significant differences were clearly seen despite the previous information given by the two separate suppliers of the active substance—this was a very surprising, unexpected result from previous literature available.

The second, and extremely important practical difference from a product formulation/optimisation perspective, is that this set of experiments resulted in a "tailing off" effect of the fixative not previously observed at the higher PMD concentrations.

Therefore, the choice of the optimum levels of fixative added can vary significantly dependent on PMD concentration and the formulation.

Figure 10:
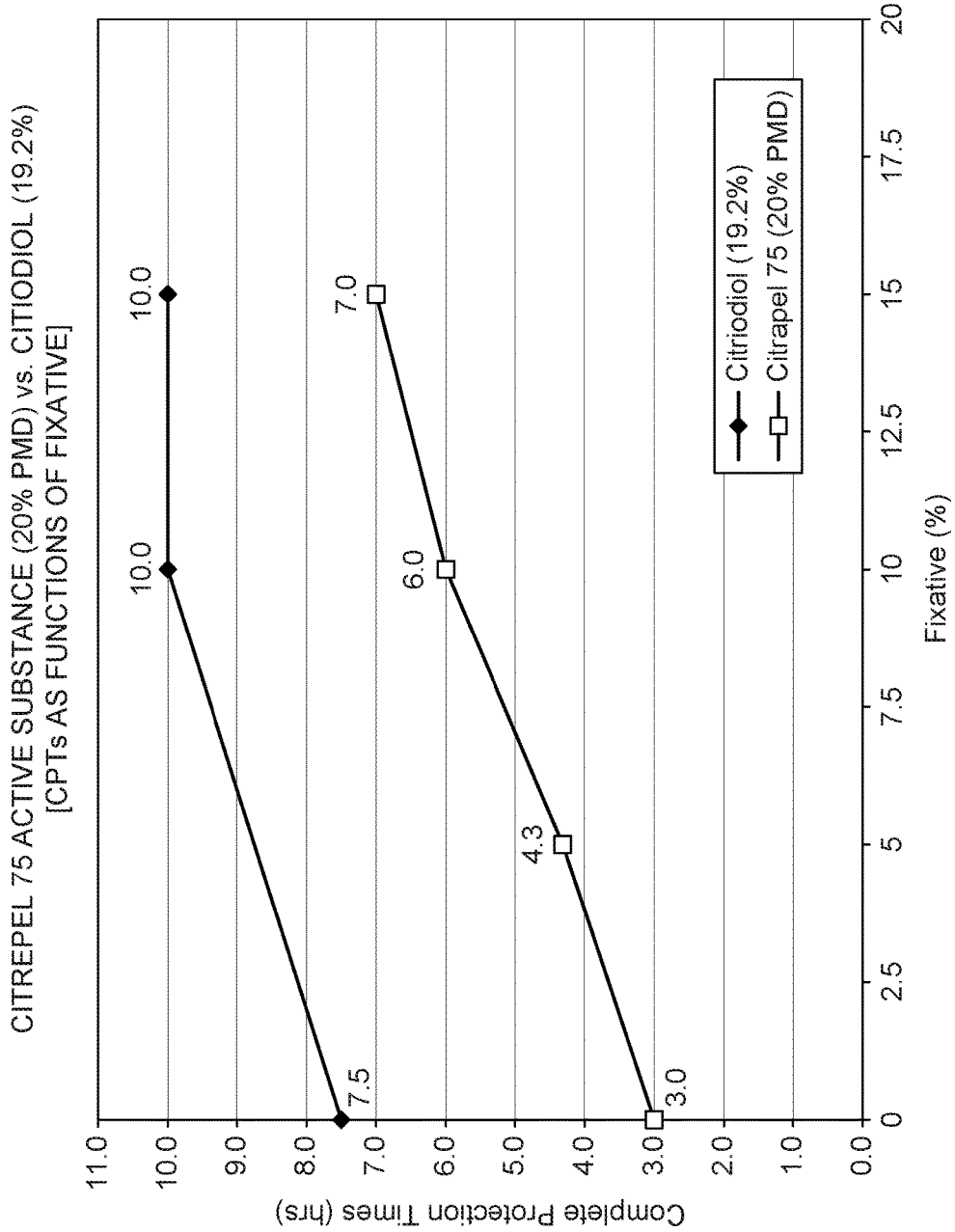
FIG. 10: CPTs with "Citriodiol" and "Citrepel" 75.

The results in FIG. 10 would suggest that the second PMD active, called "Citriodiol", offers greater protection than the other, "Citrepel 75", when combined in this new type of formulation.

To assess the extent of the interactions between "Citriodiol" and vanillin, the CDIs of the two 15% vanillin combinations were calculated, once again, as shown below.

Coefficient of drug interactions (CDI):
CDI=AB COMBO/A×B
If CDI=<1 synergy
If CDI=<0.7 significant synergy
If CDI=1, then the effect is additive
If CDI=>1 then this shows antagonism.
Figures for Calculation
  Vanillin @ 15% [i.e. $V_{15}$]=2.5 hours
  "Citriodiol" @ 20%=5.0 hours [$C_{20}$%]
  "Citriodiol" @ 30%=7.5 hours [$C_{30}$%]
  Combination 1 [$C_{20}$% $V_{15}$]=9.0 hours
  Combination 2 [$C_{30}$% $V_{15}$]=10.0 hours
Synergy Calculations
  1. $C_{20}$% $V_{15}$ Combination=9/2.5×5.0=0.72 (synergy).
  2. $C_{30}$% $V_{15}$ Combination=10/2.5×7.5=0.53 (significant synergy).

It appears that "Citriodiol" offers the possibility of reducing the final optimum PMD concentration whilst also offering a product with a 12 hour CPT.

Example 4—Stability Tests

One of the potential problems that the inventors experienced with the use of vanillin, were its photosensitisation and susceptibility to discolouration. This needed to be addressed if the inventors were to be able to move forward with the synergistic results that they achieved as a result of the vanillin inclusion.

Compositions according to the present invention including vanillin (but no additive to prevent discoloration) were exposed to the first stabilised testing conditions outlined by the current Biocide Products Regulations 528/2012. The front line accelerated conditions recommend testing at 54° C. for 14 days (see BPR 528/2012: Volume I. Part A, Chapter III: Requirements for Biocide Products, Version 1.1 Nov. 2014).

Figure 11:
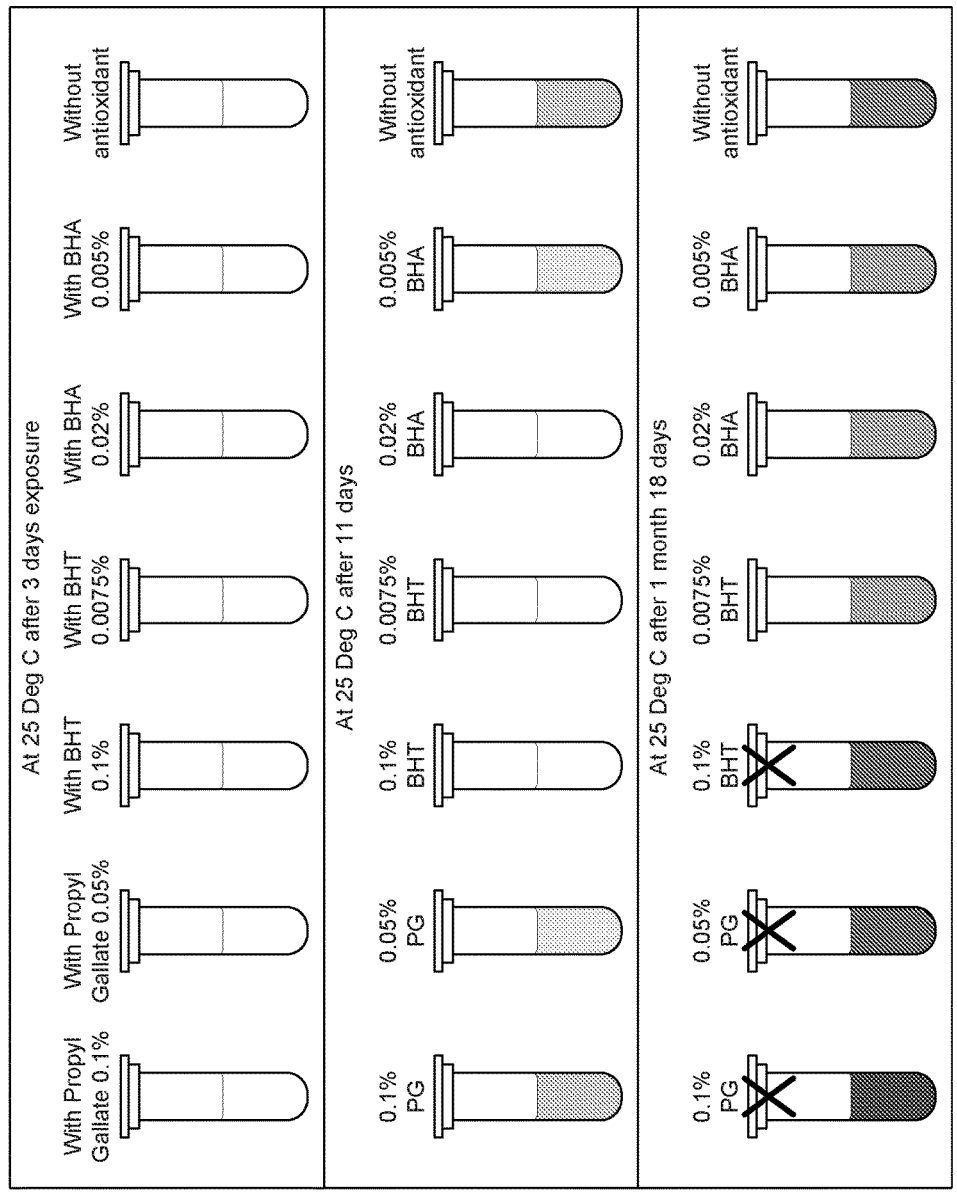
FIGS. 11 and 12: Photosensitisation and secondary oxidation of the vanillin were seen at both room temperature and 54° C.
Figure 12:
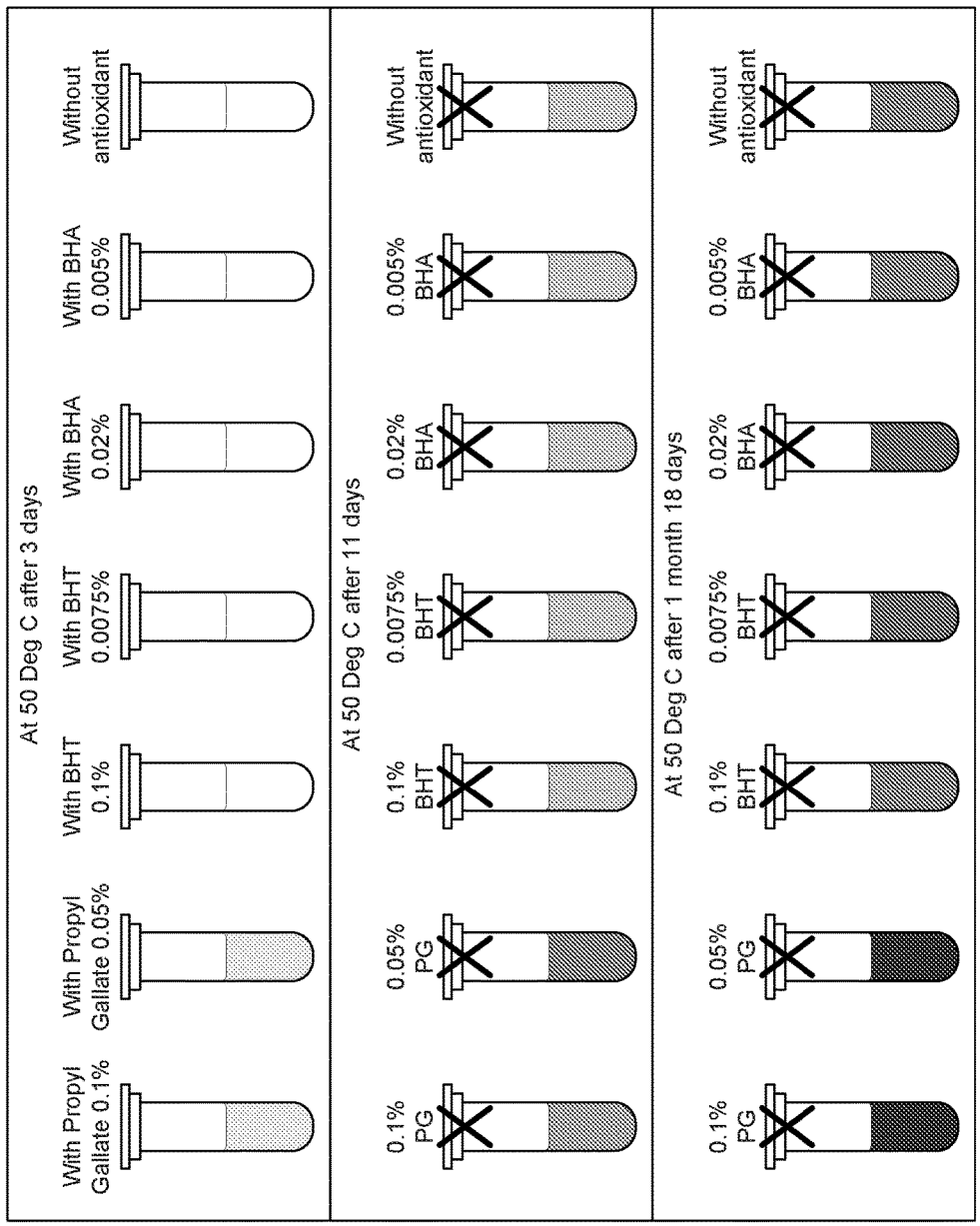

Photosensitisation and secondary oxidation of the vanillin were seen at both room temperature and 54° C. as illustrated in FIGS. 11 and 12.

Figure 13:
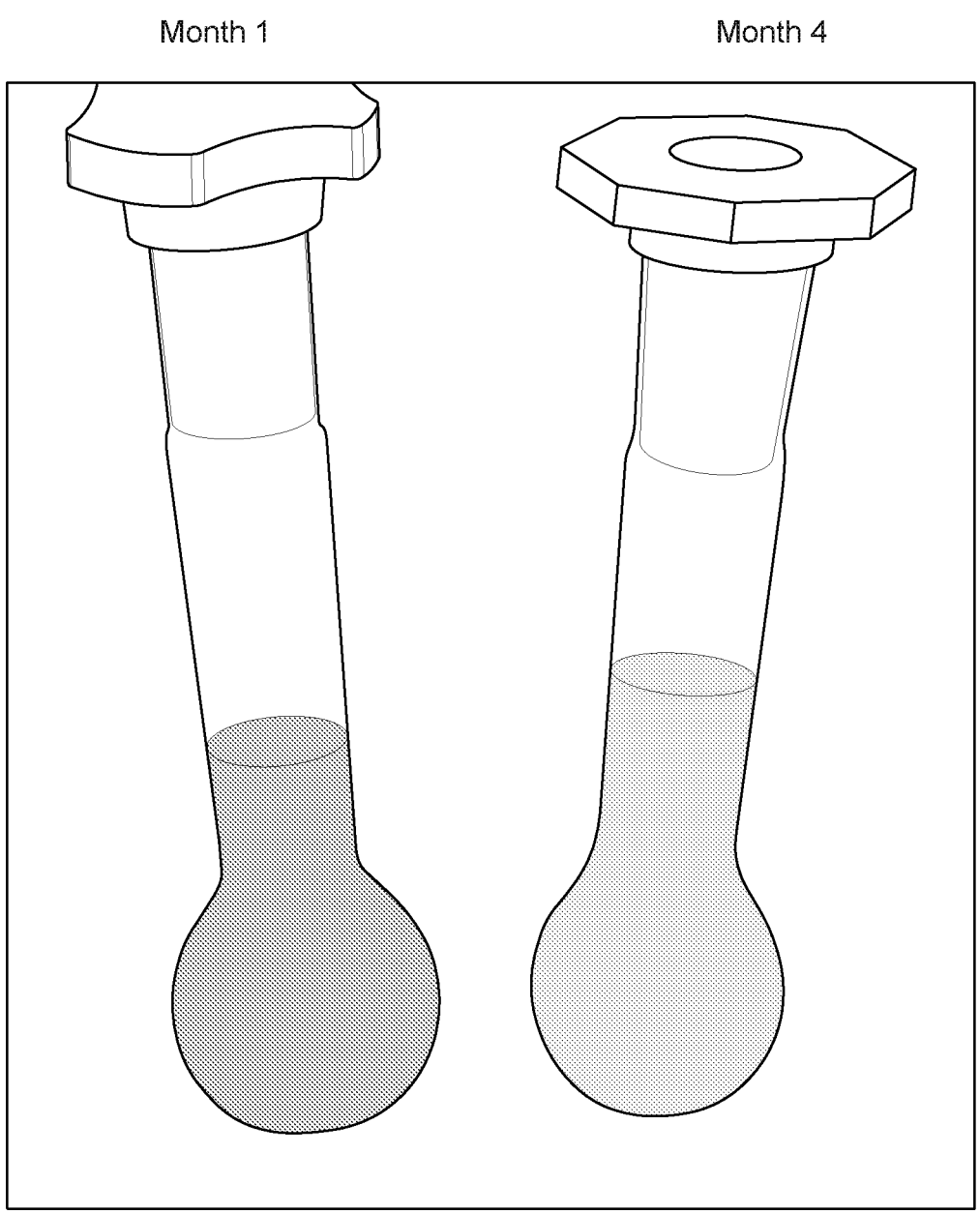
FIG. 13: Lack of photosensitisation and secondary oxidation of vanillin in the presence of sodium bisulphite.

Consequently, a series of other tests were undertaken with a variety of currently favoured antioxidants, including BHA, BHT and propyl gallate results were also negative with a number of these proven antioxidants with one significant exception, namely sodium bisulphite, as demonstrated in FIG. 13.

Figure 14:
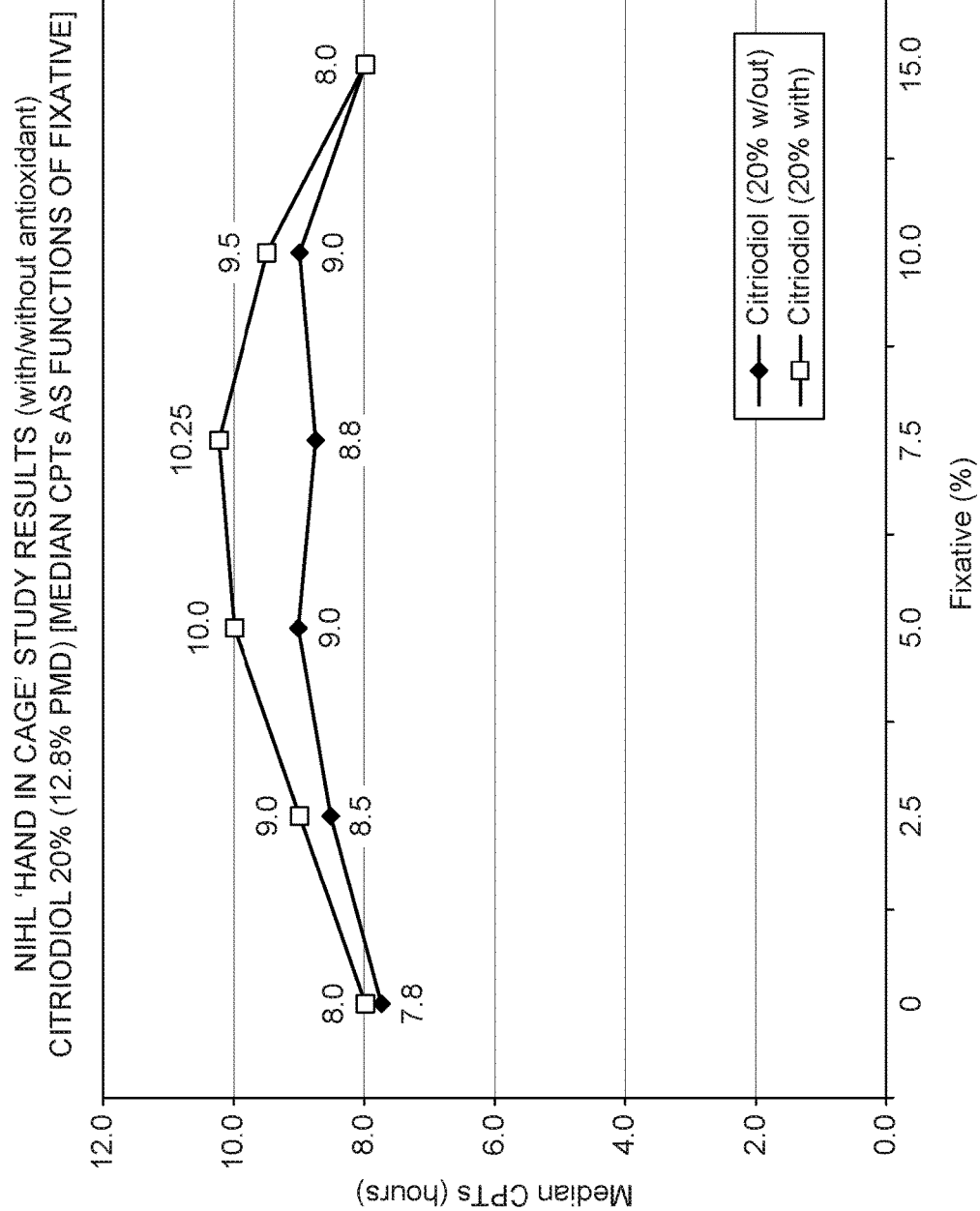
FIG. 14: CPTs with "Citriodiol", vanillin and sodium bisulphite.

In view of the above results with sodium bisulphite, further tests were undertaken with "Citriodiol" as the active substance. The aim of the new efficacy studies was to confirm that the addition of 1% antioxidant had no detrimental effect on efficacy. It was even more surprising to find that a still further significant improvement in efficacy was demonstrated as shown in FIG. 14.

This totally unexpected improvement in CPTs clearly demonstrates the dual advantage of adding the preferred excipient, sodium bisulphite, to the final optimised formulation, i.e. an additional effect to its anticipated antioxidant properties.

Although the exact mechanism of this unexpected effect has not been fully elucidated yet, sodium bisulfite most likely reacts with vanillin to form adducts. This is a very different mechanism to the way other antioxidants, such as tocopherol, would potentially stabilise vanillin.

Example 5—Tests with Higher Concentrations of "Citriodiol" (40% and 47%)

Figure 15:
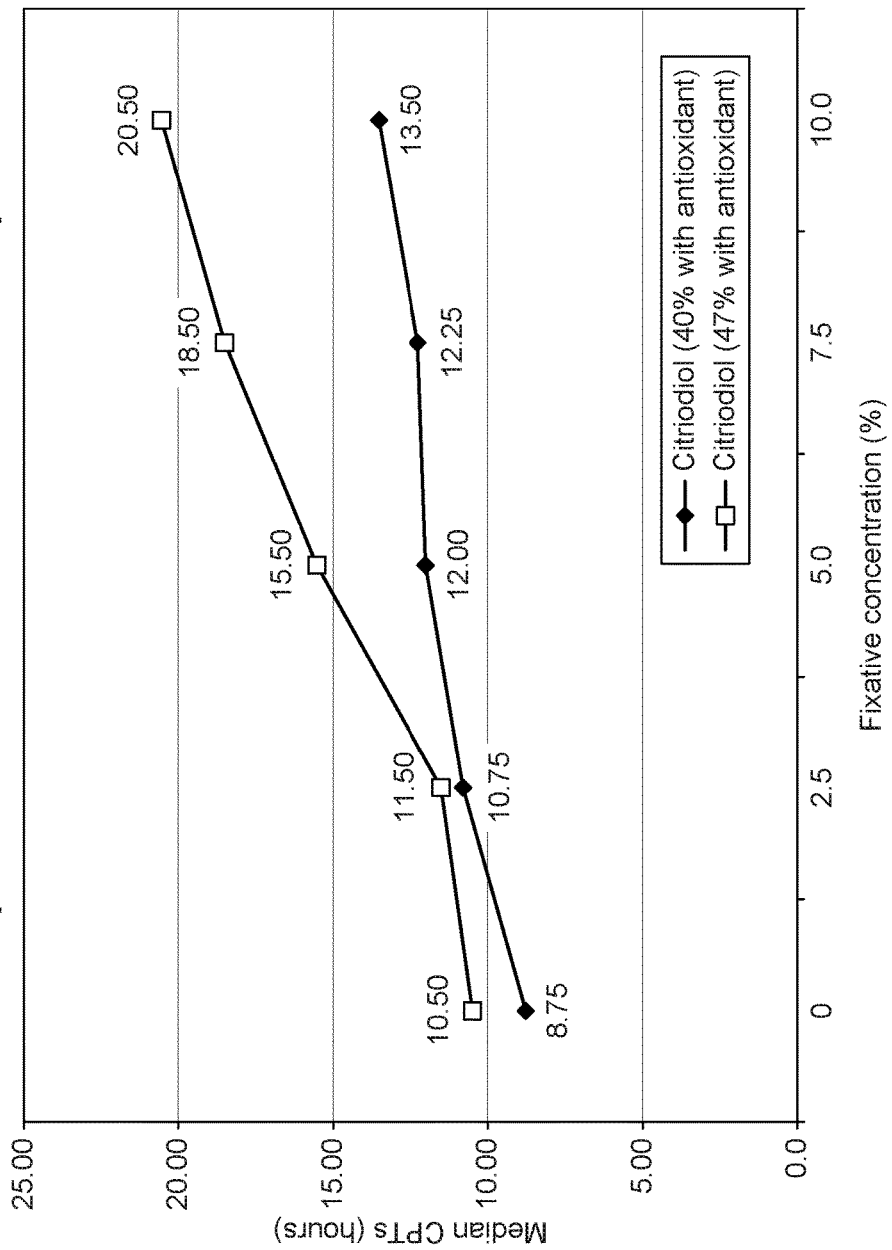
FIGS. 15 and 16: CPTs with different concentrations of PMD, vanillin and sodium bisulphite.
Figure 16:
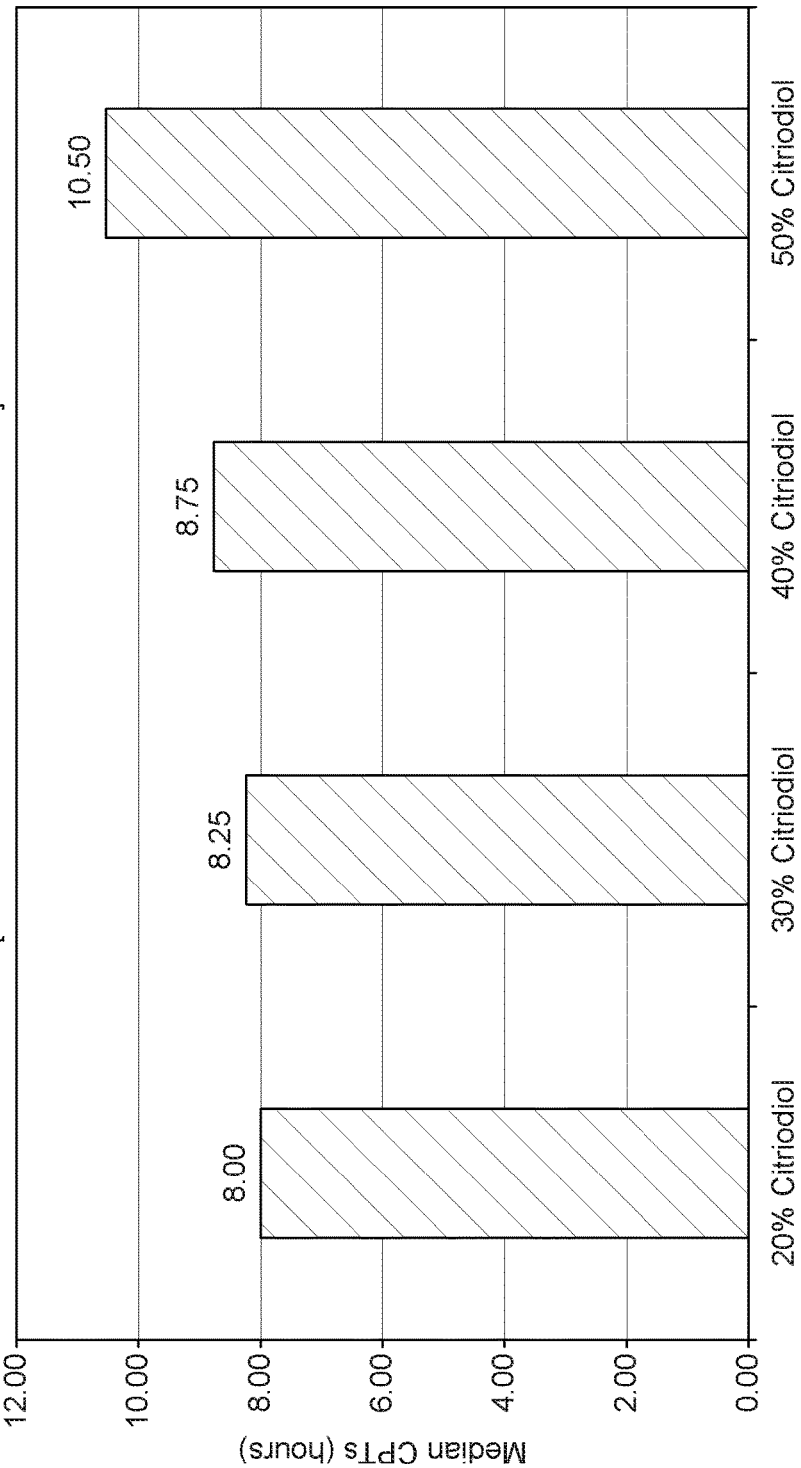

In addition to demonstrating protection times (CPTs) way above any others seen previously with natural repellents (including PMD itself), the results with 40 and 47% "Citriodiol" as illustrated in FIGS. 15 and 16 exceed those every demonstrated with synthetic chemicals (including DEET itself).

The obvious conclusion from these results is that CPTs considerably above the original target of 12 hours can be achieved using "Citriodiol" active substance at concentrations of 40% (circa 25.6% PMD) and 47% (circa 30% PMD). Such CPTs are evidently many hours ahead of the results previously seen with PMD or any other natural repellent combination, the vast majority of synthetic formulations, including DEET itself.

Summary of Examples (*Aedes Aegypti* Species)

Therefore to summarise, the above Examples versus the *Aedes Aegypti* species have confirmed certain unequivocal results, including the key one that vanillin in medium concentrations (<15%) can act as a highly effective fixative and prolong the repellent action of PMD way beyond 6 hours to achieve 12 hours or more repellency.

Example 6—Efficacy Tests (Hand in Cage) with the *Culex* Mosquito Vector

A test was undertaken against a different mosquito vector species, *Culex*, which has caused considerable damage in the USA; it is the vector which is linked to the problematic West Nile virus.

Unlike the *Aedes Aegypti* vector species, *Culex* is predominantly a "night biter" so these tests were undertaken with volunteers who remained in the laboratory overnight.

The test formulation selected for this experiment was the "Citriodiol" 40%/vanillin 10% formulation which had been previously investigated in the *Aedes* test programme. Formulations were prepared as follows.

| Formulation No | IPA | Water | 1% Sodium Bisulphite (35% IPA:65% water) | Approx 40% Citriodiol in gms (w/w) | PMD content (%) in citriodiol | Enhancer | Species & number of mosquitoes in cage | Hours of Repellancy (average of 4 volunteers) | 1 | 2 | 3 | 4 | Median |
|---|---|---|---|---|---|---|---|---|---|---|---|---|---|
| 27 | 43.11 | 5.39 | 5.39 | 36.11 | 25.6 | 10 | *Culex*. 200 nos. Biting peak time 10 p.m-6 a.m | 15 | 15 | 15 | 15.5 | 14.5 | 15 |

Figure 17:
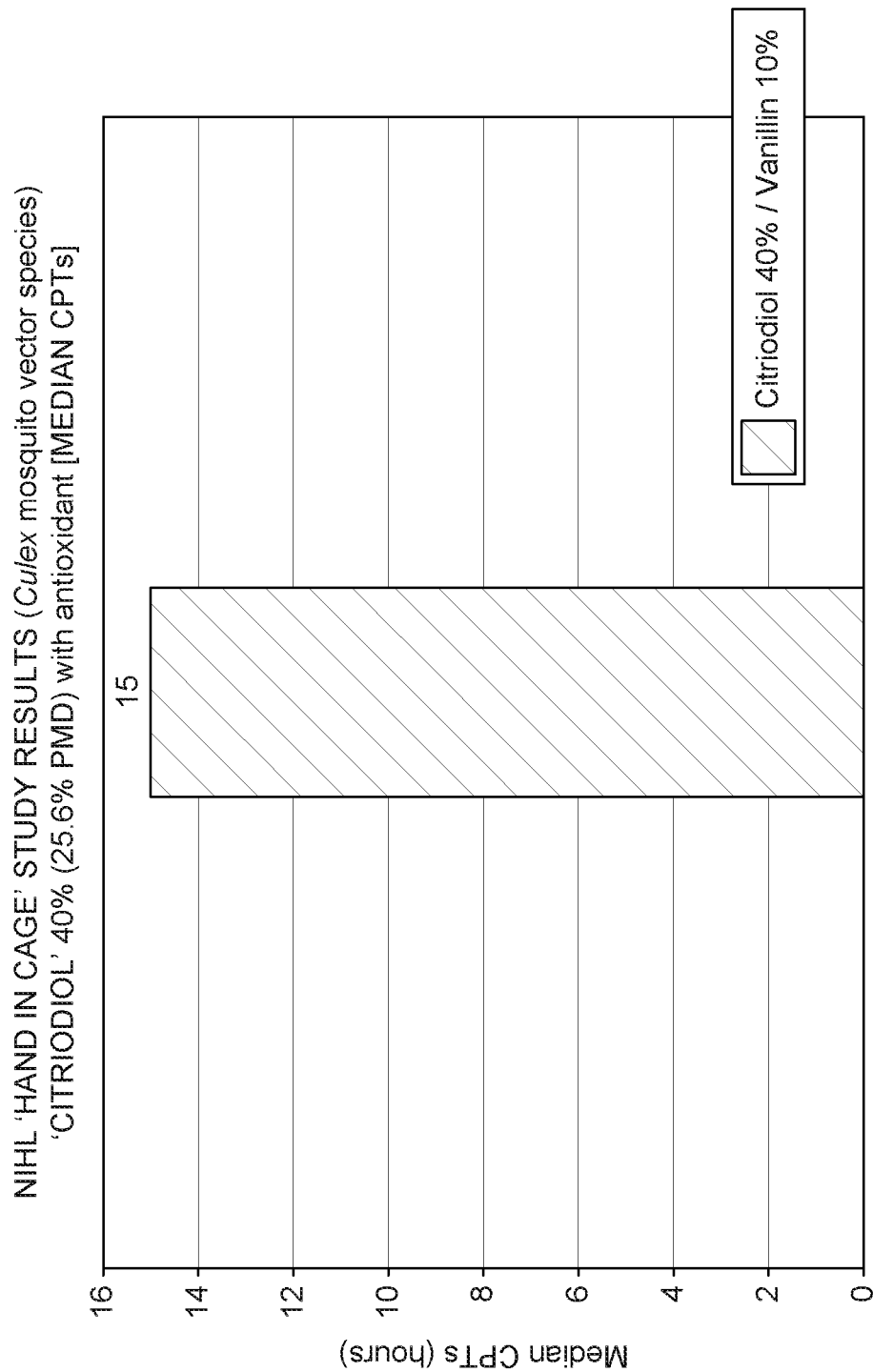
FIG. 17: This illustrates CPTs with 40% "Citriodiol" and 10% vanillin against the *Culex* mosquito vector species.

The median CPT observed against *Culex* is also shown in FIG. 17. It can be seen that the prolonged action technology used with PMD gives further positive protection results versus *Culex* since the level of protection is indeed above 12 hours with the median CPT result at 15 hours.

The sample preparation and test protocol were as follows:
Sequence Followed for Sample Preparation:
Sodium bisulphite solution was prepared by dissolving 1 gm sodium bisulphite (CAS No 7631-90-5) in 65 gm water and 35 gm IPA (isopropyl alcohol, CAS no-67-63-0) and a clear solution was obtained by stirring it for 15-20 minutes.
Sequence of Addition:
IPA+"Citriodiol" (containing 70.9% PMD) were stirred for 5 minutes.
Water was added, followed by vanillin (Code140821000). The mixture was stirred for 15 minutes.
1% sodium bisulphite solution was added and the mixture stirred for 10-15 minutes to obtain a clear solution
Method for Hand in Cage Study:
Female adult *Aedes Aegypti* mosquitoes fed on 10% sucrose and no blood meal before the test were used for the studies.
Complete protection time provided by each product was evaluated by following hand in cage studies as per a modified WHO protocol (HTM/NTD/WHOPES/2009.4).
Typically, the test consisted of inserting a repellent treated arm into a cage measuring 35 cm on each side, containing laboratory bred 200 numbers of non-blood fed *Aedes Aegypti* mosquitoes which were approximately 5-7 days old and the elapsed time to first landing or probing (which refers to an insect landing and penetrating the skin with its mouthparts, without ingesting blood) was determined.
All the products that were procured were masked and coded before handing over for testing.
In case of sprays/lotions 1 gm of product was applied to 600 square cm of the area between wrist and elbow of the forearm skin of test subjects.
The cages were placed in 30 cubic meter glass chamber wherein the ambient temperature was maintained at 27±2° C. and relative humidity of 80±10%.

Tests were conducted during day time with 4-6 number of volunteers with equal number of each gender. In case of *Culex* mosquitoes tests were conducted from dusk until dawn, which is the peak biting time of this species of mosquitoes. The volunteers were in the age group of 22 to 50 years and were selected based on signed informed consent prior to participation. Test subjects were instructed to avoid alcohol, caffeine and fragrance products 12 hours before and during the test. For treated and untreated subjects the forearms were washed with unscented soap, rinsed with water and then washed with solution of 70% alcohol and 30% water and dried with a clean towel. After application of the repellent, subjects were instructed not to rub, touch or wet the treated arm. Subjects were seated in a hall with temperature maintained at 27±2° C. and relative humidity of around 80±10% to avoid excessive heat and sweating.

Readiness of the mosquitoes to bite (biting pressure) was checked by inserting un-treated arm for 1 minute prior to inserting treated arm at each 30-minute interval. A separate cage for the un-treated (control) volunteer's arm and test subjects was maintained for checking biting pressure. Five or more landings in one minute on untreated arm was considered the right threshold to initiate the test with treated arm. Test was conducted at intervals of 30 minutes by holding the treated arm in the cage containing mosquitoes for 3 minutes, to determine landing or probing activity. This procedure was continuously repeated every 30 minutes until the first landing or probing was observed. Complete protection time was calculated as the number of minutes (or hours) elapsed between the time of repellent application and the first mosquito landing or probing. Complete Protection Time (CPT) was reported as a median value of protection time given by each individual.

Example 7—Composition According to the Present Invention

A composition according to the present invention was prepared on the basis of the following.
"Citriodiol" 40% (PMD—minimum 25%)
Vanillin 10%
Isopropyl alcohol circa 40%
Sodium bisulfate 1%
Water to 100%.

REFERENCES

1. Rodriguez S D et al. The Efficacy of Some Commercially Available Insect Repellents for *Aedes Aegypti* (Diptera: Culicidae) and *Aedes albopictus* (Diptera: Culicidae). J. Insect Sci. (2015) 15(1)
2. Goodyear et al. Expert Review of the Evidence Base for Arthropod Bite Avoidance. Journal of Travel Medicine 2010; Volume 17 (Issue 3): 182-192
3. Gupta et al. Laboratory Evaluation of Controlled-Release Repellent Formulations on Human Volunteers Under Three Climatic Regimens. Journal of the American Mosquito Control Association VoL. 5, No. I March 1989
4. Khan et al. Addition of Vanillin to Mosquito Repellents to Increase Protection Time. Mosquito News June 1975. Vol 35 No. 2 p 223-225
5. Goodyear et al. Short Report: The Safety and Toxicity of Insect Repellents. Am. J. Trop. Med. Hyg., 59(2), 1998, pp. 323-324
6. Hill et al. Randomised, double-blind control trial of p-menthane diol repellent against malaria in Bolivia. BMJ 2007; 335:1023.
7. Buescher et al. The Dose-Persistence Relationship of DEET Against *Aedes Aegypti*. Mosquito News Vol. 43, No. 3 1983.
8. Maia et al. Plant-based insect repellents: a review of their efficacy, development and testing. Malaria Journal 2011, 10(Suppl 1): S11
9. Carroll et al. a registered botanical mosquito repellent with DEET-like efficacy. J Am Mosq Control Assoc 2006; 22:507-514.
10. Moore et al. Field Evaluation of three plant-based insect repellents against malaria vectors in Vaca Diez Province, the Bolivian Amazon. J Am Mosq Control Assoc. 2002 June; 18(2):107-10
11. Trigg et al. Evaluation of a *Eucalyptus*-based Repellent Against *Anopheles* Spp. In Tanzania. Journal of American Mosquito Control Association, 12(2):243-246, 1996
12. Govere et al. Efficacy of three insect repellents against the malaria vector *Anopheles arabiensis*. Medical and Veterinary Entomology (2000) 14, 441-444
13. Barnard et al. Laboratory evaluation of mosquito repellents against *Aedes albopictus, Culex nigripalpus*, and *Ochlerotatus triseriatus* (Diptera: Culicidae). J Med Entomol 2004; 41:726-730.
14. Trigg et al. Laboratory evaluation of a *eucalyptus* based repellent against four biting arthropods. Phytother Res 1996; 10:313-316.
15. Durnez et al. Residual Transmission of Malaria: An Old Issue for New Approaches. Intech Open Access Article 2013.

What is claimed is:

1. An insect repellent composition which provides a complete protection time of at least 8 hours, the composition comprising p-methane-3,8-diol in an amount of at least 20% by weight of the composition, vanillin in an amount of 5 to 15% by weight of said composition, an antioxidant that prevents discoloration of said vanillin when said composition is stored at 54° C. for 14 days and a delivery vehicle.

2. An insect repellent composition according to claim 1 comprising p-methane-3,8-diol as the sole insect repellent, vanillin and a delivery vehicle.

3. An insect repellent composition comprising p-methane-3,8-diol as the sole insect repellent in an amount of at least 20% by weight of the composition, vanillin and a delivery vehicle, wherein said insect repellent composition provides a complete protection time of at least 8 hours.

4. An insect repellent composition according to claim 3 comprising p-methane-3,8-diol, vanillin and a delivery vehicle, for once or bi-daily administration.

5. An insect repellent composition according to claim 1, for the prevention of a disease state selected from the group consisting of; disease states caused by *Aedes Aegypti*, Dengue fever, Yellow fever and the Zika virus.

6. An insect repellent composition according to claim 3, for the prevention of a Disease state selected from the group consisting of: disease states caused by *Aedes Aegypti*, Dengue fever, Yellow fever and the Zika virus.

7. An insect repellent composition according to claim 3 comprising p-methane-3,8-diol, vanillin and a delivery vehicle, for the prevention of a disease state caused by the *Culex* mosquito.

8. An insect repellent composition according to claim 3 comprising p-methane-3,8-diol, vanillin, and a delivery vehicle, for repelling midges, including the Scottish Highland midge (Meanbh-chuileag).

9. An insect repellent composition according to claim 3, which further comprises an antioxidant that prevents discoloration of said vanillin when said composition is stored at 54° C. for 14 days.

10. An insect repellent composition according to claim 1, wherein said antioxidant comprises sodium bisulphite.

11. An insect repellent composition according to claim 10, wherein said sodium bisulphite is present in an amount of about 0.5 to about 1.5% weight % of the composition.

12. An insect repellent composition according to claim 1, wherein p-methane-3,8-diol is present as the sole insect repellent.

13. An insect repellent composition according to claim 1, wherein said composition provides a complete protection time of at least 10 hours.

14. An insect repellent composition according to claim 1, wherein said composition provides a complete protection time of at least 12 hours.

15. An insect repellent composition according to claim 1, for once or bi-daily administration.

16. An insect repellent composition according to claim 1, for the prevention of a disease state selected from the group consisting of: disease states caused by the *Culex* mosquito, and West Nile virus.

17. An insect repellent composition according to claim 1, for repelling midges, including Scottish Highland midge (Meanbh-chuileag).

18. An insect repellent composition according to claim 1, wherein said vanillin is present in an amount of 10-% by weight of said composition.

19. An insect repellent composition according to claim 1, which said p-methane-3,8-diol is present in an amount of at least 25% by weight of said composition.

20. An insect repellent composition according to claim 1, which said p-methane-3,8-diol is present in an amount of at least 30% by weight of said composition.

21. An insect repellent composition according to claim 1, wherein said delivery vehicle comprises isopropyl alcohol.

22. An insect repellent composition according to claim 1 that comprises p-methane-3,8-diol, vanillin, sodium bisulfite, water and isopropyl alcohol.

23. An insect repellent composition according to claim 22, wherein said isopropyl alcohol is present in an amount of about 40% by weight of said composition.

24. An insect repellent composition according to claim 1, which is a spray, lotion, gel or roll-on.

25. An article of manufacture, such as a mosquito net or a dermal wipe, that is impregnated with a composition according to claim 1.

26. A method of preventing a disease state selected from the group consisting of: disease states caused by a biting fly, disease states caused by *Aedes Aegypti*, Dengue fever, Yellow fever and the Zika virus; of repelling a biting fly, which method comprises administering to the skin of a user a composition according to claim 1.

27. A method according to claim 26, for the prevention of a disease state selected from the group consisting of: disease states caused by the *Culex* mosquito, and West Nile virus.

28. A method according to claim 26, for repelling midges, including the Scottish Highland midge (Meanbhchuileag).

29. A method of repelling insects comprising administering to the skin of a user a composition according to claim 1.

30. A method of repelling insects comprising administering to the skin of a user a composition according to claim 3.

* * * * *

UNITED STATES PATENT AND TRADEMARK OFFICE
CERTIFICATE OF CORRECTION

PATENT NO. : 10,064,407 B2
APPLICATION NO. : 15/671712
DATED : September 4, 2018
INVENTOR(S) : John Hywel Davies et al.

Page 1 of 1

It is certified that error appears in the above-identified patent and that said Letters Patent is hereby corrected as shown below:

On the Title Page

Item (72), replace "John Hywel Davies, Odiham (GB)" with --John Hywel Davies, The Algarve, (PT)--

Signed and Sealed this
Fourth Day of December, 2018

Andrei Iancu
*Director of the United States Patent and Trademark Office*